US007547720B2

(12) United States Patent
Doherty et al.

(10) Patent No.: US 7,547,720 B2
(45) Date of Patent: Jun. 16, 2009

(54) OPHTHALMIC COMPOSITIONS FOR TREATING OCULAR HYPERTENSION

(75) Inventors: James B. Doherty, Montvale, NJ (US); Meng-Hsin Chen, Westfield, NJ (US); Luping Liu, Plainsboro, NJ (US); Swaminathan R. Natarajan, Scotch Plains, NJ (US); Robert M. Tynebor, Woodbridge, NJ (US)

(73) Assignee: Merck & Co. Inc., Rahway, NJ (US)

( * ) Notice: Subject to any disclaimer, the term of this patent is extended or adjusted under 35 U.S.C. 154(b) by 8 days.

(21) Appl. No.: 11/641,212

(22) Filed: Dec. 19, 2006

(65) Prior Publication Data

US 2007/0129418 A1 Jun. 7, 2007

(51) Int. Cl.
*A61K 31/416* (2006.01)
*C07D 231/56* (2006.01)

(52) U.S. Cl. .................................. 514/406; 548/362.5
(58) Field of Classification Search ................. 548/113, 548/362.5; 514/406
See application file for complete search history.

(56) References Cited

U.S. PATENT DOCUMENTS

| 4,690,931 A | 9/1987 | Wick et al. |
| 5,151,444 A | 9/1992 | Meno et al. |
| 5,296,504 A | 3/1994 | Stjernschantz et al. |
| 5,348,968 A | 9/1994 | Lavielle et al. |
| 5,352,708 A | 10/1994 | Woodward et al. |
| 5,422,368 A | 6/1995 | Stjernschantz et al. |
| 5,573,758 A | 11/1996 | Adorante et al. |
| 5,889,052 A | 3/1999 | Klinko et al. |
| 5,925,342 A | 7/1999 | Adorante et al. |
| 6,956,036 B1 | 10/2005 | May et al. |

FOREIGN PATENT DOCUMENTS

| EP | 1 114816 A1 | 9/1999 |
| WO | WO 94/13275 A1 | 6/1994 |
| WO | WO 94/28900 A1 | 12/1994 |
| WO | WO 96/33719 A1 | 10/1996 |
| WO | WO 89/10757 A1 | 11/1998 |
| WO | WO 01 52876 A1 | 1/2000 |
| WO | WO 01 70701 A1 | 11/2000 |
| WO | WO 01/46140 A1 | 6/2001 |
| WO | WO 01/70702 A1 | 9/2001 |
| WO | WO 01/72268 A1 | 10/2001 |
| WO | WO 02/24647 A2 | 3/2002 |
| WO | WO 02/42268 A2 | 5/2002 |
| WO | WO 03011833 A1 | 2/2003 |

OTHER PUBLICATIONS

Wiederholt et al. (Progress in Retinal & Eye Research 2000, 19(3), 271-295).*
Harman et al., "Development and Aging of Cell Topography in the Human Retinal Pigment Epithelium", 1997, pp. 2016-2026, vol. 38, Investigative Ophthalmology & Visual Science.
Berge et al., "Pharmaceutical Salts", 1977, pp. 1-19, vol. 66, Journal of Pharmaceutical Sciences.
Hanner et al., "The β Subunit of High Conductance Calcium-Activated Potassium Channel", 1998 pp. 16283-16296, vol. 273, J. Biol. Chem.
Vasallo et al., "Expression of Na,K-ATPase Alpha Subunit Isoforms in the Human Ciliary Body and Cultured Ciliary Epithelial Cells", 1989, pp. 243-252, vol. 141, Journal of Cellular Physiology.
Ero et al., "New Antifungal 1,2,4-Triazoles with Difluoro (heteroaryl) methyl Moiety", 2000, pp. 982-990, vol. 48, Chem. Pharm. Bull.
Y. Hirai et al., Japan Patent 89-207208 (Chemical Abstract, 1990 112, 32154a).
T. Morie et al., "Convenient Synthesis of N-(2,2-Dimethyl-1,3-Dioxan-5-YL)-1H-Indazole-3-Carboxamide, the Intermediate of 5-HT3 Receptor Antagonist", 1997, pp. 559-566, vol. 27 (4), Synthetic Communications.
T. Yoshida et al., "Practical Synthesis of 1H-INdazole-3-Carboxylic Acid and its Derivatives", 1996, pp. 2701-2712, vol. 27 (4), Heterocycles.
Beilstein Regisry No. 91608, XP-002275106. 1965.
Beilstein Registry No. 144953, XP-002275105, 1920.
Beilstein Registry No. 888594, XP-002275104, 1972.
Beilstein Registry No. 224495, XP-002275107, 1924.

* cited by examiner

*Primary Examiner*—Rebecca L Anderson
*Assistant Examiner*—Jason Nolan
(74) *Attorney, Agent, or Firm*—Sylvia A. Ayler; William Krovatin

(57) ABSTRACT

This invention relates to potent potassium channel blocker compounds of Formula I or a formulation thereof for the treatment of glaucoma and other conditions which leads to elevated intraocular pressure in the eye of a patient. This invention also relates to the use of such compounds to provide a neuroprotective effect to the eye of mammalian species, particularly humans.

4 Claims, No Drawings

OPHTHALMIC COMPOSITIONS FOR TREATING OCULAR HYPERTENSION

This claims the benefit of U.S. Provisional Application 60/424,808 and 60/500,091.

BACKGROUND OF THE INVENTION

Glaucoma is a degenerative disease of the eye wherein the intraocular pressure is too high to permit normal eye function. As a result, damage may occur to the optic nerve head and result in irreversible loss of visual function. If untreated, glaucoma may eventually lead to blindness. Ocular hypertension, i.e., the condition of elevated intraocular pressure without optic nerve head damage or characteristic glaucomatous visual field defects, is now believed by the majority of ophthalmologists to represent merely the earliest phase in the onset of glaucoma.

There are several therapies for treating glaucoma and elevated intraocular pressure, but the efficacy and the side effect profiles of these agents are not ideal. Recently potassium channel blockers were found to reduce intraocular pressure in the eye and therefore provide yet one more approach to the treatment of ocular hypertension and the degenerative ocular conditions related thereto. Blockage of potassium channels can diminish fluid secretion, and under some circumstances, increase smooth muscle contraction and would be expected to lower IOP and have neuroprotective effects in the eye. (see U.S. Pat. Nos. 5,573,758 and 5,925,342; Moore, et al., Invest. Ophthalmol. Vis. Sci 38, 1997; WO 89/10757, WO94/28'900, and WO 96/33719).

SUMMARY OF THE INVENTION

This invention relates to the use of potent potassium channel blockers or a formulation thereof in the treatment of glaucoma and other conditions which are related to elevated intraocular pressure in the eye of a patient. This invention also relates to the use of such compounds to provide a neuroprotective effect to the eye of mammalian species, particularly humans. More particularly this invention relates to the treatment of glaucoma and/or ocular hypertension (elevated intraocular pressure) using novel indazole compounds having the structural formula I:

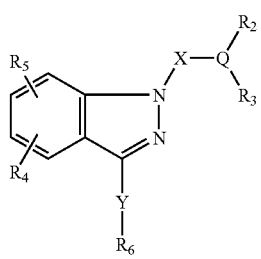

Formula I or a pharmaceutically acceptable salt, enantiomer, diasteromer or mixture thereof:

wherein,

R represents hydrogen, or $C_{1-6}$ alkyl;

X represents $-(CHR_7)_p-$, $-(CHR_7)_pCO-$;

Y represents $-CO(CH_2)_n-$, $CH_2$, or $-CH(OR)-$;

Q represents $CR^y$;

$R^y$ represents H, or $C_{1-6}$ alkyl;

$R_w$ represents H, $C_{1-6}$ alkyl, $-C(O)C_{1-6}$ alkyl, $-C(O)OC_{1-6}$ alkyl, $-SO_2N(R)_2$, $-SO_2C_{1-6}$ alkyl, $-SO_2C_{6-10}$ aryl, $NO_2$, CN or $-C(O)N(R)_2$;

$R_2$ represents hydrogen, $C_{1-10}$ alkyl, OH, $C_{2-6}$ alkenyl, $C_{1-6}$ alkylSR, $-(CH_2)_nO(CH_2)_mOR$, $-(CH_2)_nC_{1-6}$ alkoxy, $-(CH_2)_nC_{3-8}$ cycloalkyl, $-(CH_2)_nC_{3-10}$ heterocyclyl, $-N(R)_2$, $-COOR$, or $-(CH_2)_nC_{6-10}$ aryl, said alkyl, heterocyclyl, or aryl optionally substituted with 1-3 groups selected from $R^a$;

$R_3$ represents hydrogen, $C_{1-10}$ alkyl, $-(CH_2)_nC_{3-8}$ cycloalkyl, $-(CH_2)_nC_{3-10}$ heterocyclyl, $-(CH_2)_nCOOR$, $-(CH_2)_nC_{6-10}$ aryl, $-(CH_2)_nNHR_8$, $-(CH_2)_nN(R)_2$, $-(CH_2)_nN(R_8)_2$, $-(CH_2)_nNHCOOR$, $-(CH_2)_nN(R_8)CO_2R$, $-(CH_2)_nN(R_8)COR$, $-(CH_2)_nNHCOR_2$, $-(CH_2)_nCON(R_8)$, aryl, $-(CH_2)_nC_{1-6}$ alkoxy, $CF_3$, $-(CH_2)_nSO_2R$, $-(CH_2)_nSO_2N(R)_2$, $-(CH_2)_nCON(R)_2$, $-(CH_2)_nCONHC(R)_3$, $-(CH_2)_nCONHC(R)_2CO_2R$, $-(CH_2)_nCOR_8$, nitro, cyano or halogen, said alkyl, alkoxy, heterocyclyl, or aryl optionally substituted with 1-3 groups of $R^a$;

or $R_2$ and $R_3$ taken together with the intervening Q form a 3-10 membered carbocyclic or heterocyclic carbon ring optionally interrupted by 1-2 atoms of O, S, C(O) or NR, and optionally having 1-4 double bonds, and optionally substituted by 1-3 groups selected from $R^a$;

or $R_2$ and $R_3$ taken together with the intervening Q represent OR;

$R_4$ and $R_5$ independently represent hydrogen, $C_{1-6}$ alkoxy, OH, $C_{1-6}$ alkyl, COOR, $SO_qC_{1-6}$ alkyl, $COC_{1-6}$ alkyl, $SO_3H$, $-O(CH_2)_nN(R)_2$, $-O(CH_2)_nCO_2R$, $-OPO(OH)_2$, $CF_3$, $OCF_3$ $-N(R)_2$, nitro, cyano, $C_{1-6}$ alkylamino, or halogen; and $R_6$ represents hydrogen, $C_{1-10}$ alkyl, $-(CH_2)_nC_{6-10}$ aryl, $NR_cR_d$, $-NR(CH_2)_nC_{6-10}$ aryl, $-N((CH_2)_nC_{6-10}$ aryl$)_2$, $-(CH_2)_nC_{3-10}$ heterocyclyl, $-NR(CH_2)_nC_{3-10}$ heterocyclyl, $-N((CH_2)_nC_{3-10}$ heterocyclyl$)_2$ $(C_{6-10}$ aryl$)O-$, $-(CH_2)_n$ $C_{3-8}$ cycloalkyl, $-COOR$, $-C(O)CO_2R$, said aryl, heterocyclyl and alkyl optionally substituted with 1-3 groups selected from $R^a$, wherein the $R^a$(s) can be attached to any carbon atom or heteroatom selected from N and S;

$R_c$ and $R_d$ independently represent H, $C_{1-6}$ alkyl, $C_{2-6}$ alkenyl, $C_{1-6}$ alkylSR, $-(CH_2)_nO(CH_2)_mOR$, $-(CH_2)_nC_{1-6}$ alkoxy, or $-(CH_2)_nC_{3-8}$ cycloalkyl;

or $R_c$ and $R_d$ taken together with the intervening N atom form a 4-10 membered heterocyclic carbon ring optionally interrupted by 1-2 atoms of O, S, C(O) or NR, and optionally having 1-4 double bonds, and optionally substituted by 1-3 groups selected from $R^a$;

$R_7$ represents hydrogen, $C_{1-6}$ alkyl, $-(CH_2)_nCOOR$ or $-(CH_2)_nN(R)_2$, $R_8$ represents $-(CH_2)_nC_{3-8}$ cycloalkyl, $-(CH_2)_n3-10$ heterocyclyl, $C_{1-6}$ alkoxy or $-(CH_2)_nC_{5-10}$ heteroaryl, $-(CH_2)_n$ $C_{6-10}$ aryl said heterocyclyl, aryl or heteroaryl optionally substituted with 1-3 groups selected from $R^a$;

$R^a$ represents F, Cl, Br, I, $CF_3$, $N(R)_2$, $NO_2$, CN, $-O-$, $-COR_8$, $-CONHR_8$, $-CON(R_8)_2$, $-O(CH_2)_nCOOR$, $-NH(CH_2)_nOR$, $-COOR$, $-OCF_3$, $CF_2CH_2OR$, $-NH-COR$, $-SO_2R$, $-SO_2NR_2$, $-SR$, $(C_1-C_6$ alkyl$)O-$, $-(CH_2)_nO(CH_2)_mOR$, $-(CH_2)_nC_{1-6}$ alkoxy, (aryl)$O-$, $-(CH_2)_nOH$, $(C_1-C_6$ alkyl$)S(O)_m-$, $H_2N-C(NH)-$, $(C_1-$ C$_6$alkyl)C(O)—, (C$_1$-C$_6$ alkyl)OC(O)NH—, —(C$_1$-C$_6$ alkyl) NR$_w$(CH$_2$)$_n$C$_{3-10}$ heterocyclyl-R$_w$, —(C$_1$-C$_6$ alkyl)O(CH$_2$)$_n$ C$_{3-10}$ heterocyclyl-R$_w$, —(C$_1$-C$_6$ alkyl)S(CH$_2$)$_n$C$_{3-10}$ heterocyclyl-R$_w$, —(C$_1$-C$_6$ alkyl)-C$_{3-10}$ heterocyclyl-R$_w$, —(CH$_2$)$_n$—Z$^1$—C(=Z$^2$)N(R)$_2$, —(C$_{2-6}$ alkenyl)NR$_w$(CH$_2$)$_n$ C$_{3-10}$ heterocyclyl-R$_w$, —(C$_{2-6}$ alkenyl)O(CH$_2$)$_n$C$_{3-10}$ heterocyclyl-R$_w$, —(C$_{2-6}$ alkenyl)S(CH$_2$)$_n$C$_{3-10}$ heterocyclyl-R$_w$, —(C$_{2-6}$ alkenyl)-C$_{3-10}$ heterocyclyl-R$_w$, —(C$_{2-6}$ alkenyl)—Z$^1$—C(=Z$^2$)N(R)$_2$, —(CH$_2$)$_n$SO$_2$R, —(CH$_2$)$_n$ SO$_3$H, —(CH$_2$)$_n$PO(OR)$_2$, C$_{3-10}$cycloalkyl, C$_{6-10}$ aryl, C$_{3-10}$ heterocyclyl, C$_{2-6}$ alkenyl, and C$_1$-C$_{10}$ alkyl, said alkyl, alkenyl, alkoxy, heterocyclyl and aryl optionally substituted with 1-3 groups selected from C$_1$-C$_6$ alkyl, halogen, (CH$_2$)$_n$ OH, CN, NO$_2$, CON(R)$_2$ and COOR;

Z$^1$ and Z$^2$ independently represents NR$_w$, O, CH$_2$, or S;

m is 0-3;

n is 0-3;

p is 0-3 and q is 0-2.

This and other aspects of the invention will be realized upon inspection of the invention as a whole.

DETAILED DESCRIPTION OF THE INVENTION

The present invention is directed to novel potassium channel blockers of Formula I. It also relates to a method for decreasing elevated intraocular pressure or treating glaucoma by administration, preferably topical or intra-camaral administration, of a composition containing a potassium channel blocker of Formula I described hereinabove and a pharmaceutically acceptable carrier.

One embodiment of this invention is realized when p is 1-3.

Another embodiment of this invention is realized when Y is —CO(CH$_2$)$_n$ and all other variables are as originally described. A subembodiment of this invention is realized when n is 0.

Another embodiment of this invention is realized when Y is CH(OR) and all other variables are as originally described.

In another embodiment R$_w$ is selected from H, C$_{1-6}$ alkyl, —C(O)C$_{1-6}$ alkyl and —C(O)N(R)$_2$ and all other variables are as originally described.

In another embodiment X is —(CHR$_7$)$_p$—, p is 1-3 and all other variables are as originally described.

In another embodiment X is —(CHR$_7$)$_p$CO—, p is 1-3 and all other variables are as originally described.

Still another embodiment of this invention is realized when R$_6$ is C$_{1-10}$ alkyl, (CH$_2$)$_n$C$_{6-10}$ aryl, (CH$_2$)$_n$C$_{3-10}$ heterocyclyl, NR$_c$R$_d$ or (CH$_2$)$_n$C$_{3-8}$ cycloalkyl, said alkyl, aryl, heterocyclyl and cycloalkyl optionally substituted with 1 to 3 groups of R$^a$, and all other variables are as originally described.

Yet another embodiment of this invention is realized when R$_6$ is C$_{1-10}$ alkyl, (CH$_2$)$_n$C$_{6-10}$ aryl, or (CH$_2$)$_n$C$_{3-10}$ heterocyclyl, said alkyl, aryl, and heterocyclyl optionally substituted with 1 to 3 groups of R$^a$, and all other variables are as originally described.

Yet another embodiment of this invention is realized when R$_7$ is hydrogen or C$_{1-6}$ alkyl, and all other variables are as originally described.

Yet another embodiment of this invention is realized when Y is —CO(CH$_2$)$_n$, and n is 0.

Still another embodiment of this invention is realized when Y is —CO(CH$_2$)$_n$, R$_2$ is C$_{1-10}$ alkyl or C$_{1-6}$ alkylOR and R$_3$ is C$_{1-10}$ alkyl, (CH$_2$)$_n$C$_{3-10}$ heterocyclyl, X is —(CHR$_7$)$_p$CO—, and p is 1-3 said heterocyclyl and alkyl optionally substituted with 1 to 3 groups of R$^a$. A subembodiment of this invention is realized when n is 0.

Another embodiment of the instant invention is realized when R$^a$ is selected from F, Cl, Br, I, CF$_3$, N(R)$_2$, NO$_2$, CN, —O—, —CONHR$_8$, —CON(R$_8$)$_2$, —O(CH$_2$)$_n$COOR, —NH(CH$_2$)$_n$OR, —COOR, —OCF$_3$, —NHCOR, —SO$_2$R, —SO$_2$NR$_2$, —SR, (C$_1$-C$_6$ alkyl)O—, —(CH$_2$)$_n$O(CH$_2$)$_m$OR, —(CH$_2$)$_n$C$_{1-6}$ alkoxy, (aryl)O—, —OH, (C$_1$-C$_6$ alkyl)S (O)$_m$—, H$_2$N—C(NH)—, (C$_1$-C$_6$ alkyl)C(O)—, (C$_1$-C$_6$ alkyl)OC(O)NH—, —(C$_1$-C$_6$ alkyl)NR$_w$(CH$_2$)$_n$C$_{3-10}$ heterocyclyl-R$_w$, —(CH$_2$)$_n$—Z$^1$—C(=Z$^2$)N(R)$_2$, —(C$_{2-6}$ alkenyl) NR$_w$(CH$_2$)$_n$C$_{3-10}$ heterocyclyl-R$_w$, —(C$_{2-6}$ alkenyl)—Z$^1$—C (=Z$^2$)N(R)$_2$, —(CH$_2$)$_n$SO$_2$R, —(CH$_2$)$_n$SO$_3$H, —(CH$_2$)$_n$PO (OR)$_2$, C$_{2-6}$ alkenyl, and C$_1$-C$_{10}$ alkyl, said alkyl and alkenyl, optionally substituted with 1-3 groups selected from C$_1$-C$_6$alkyl, and COOR;

Examples of compounds to be used in this invention are found in Tables 1 and 2:

TABLE 1

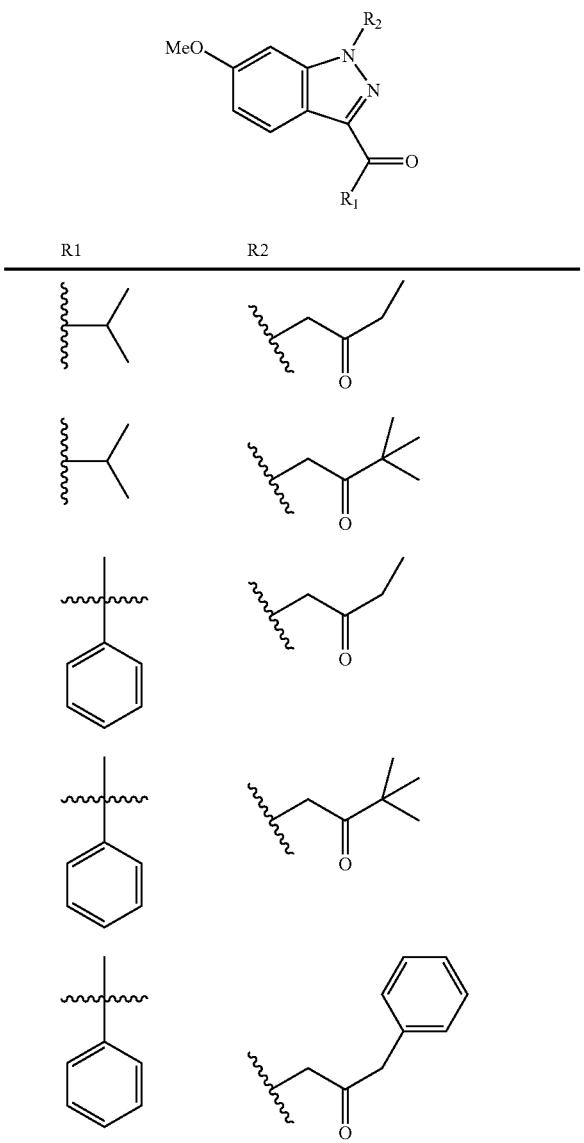

TABLE 1-continued
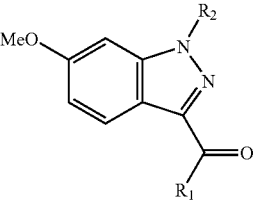
| R1 | R2 |
|---|---|
| 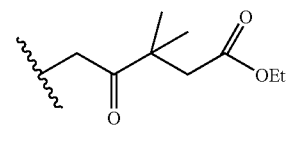 | 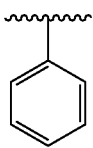 |
| 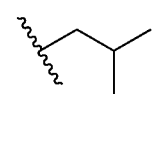 | 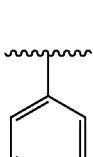 |
| 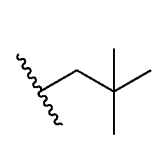 |  |
| 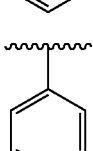 | 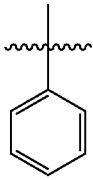 |
| 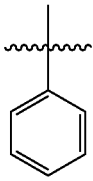 | 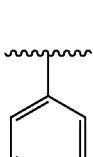 |
| 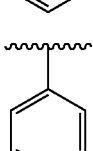 | 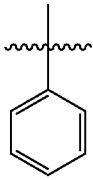 |
| 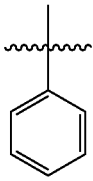 | 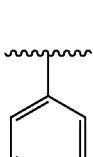 |
TABLE 1-continued
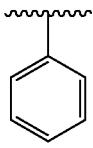
| R1 | R2 |
|---|---|
| 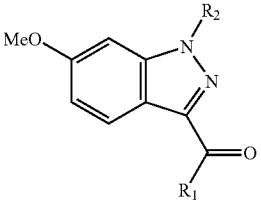 | 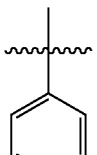 |
| 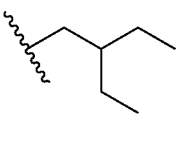 | 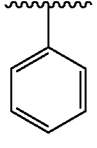 |
| 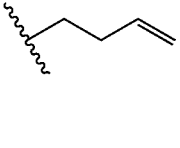 | 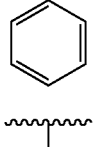 |
| 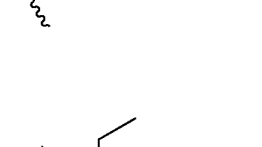 | 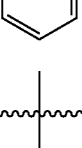 |
| 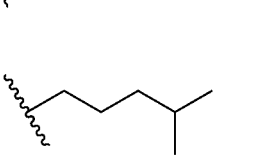 | 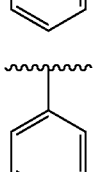 |
| 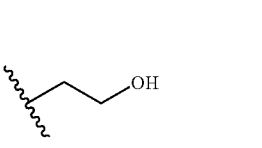 | 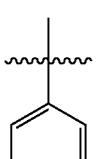 |
| 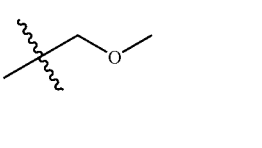 | 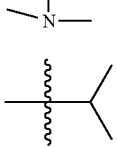 |
| 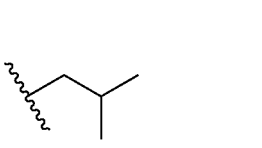 | 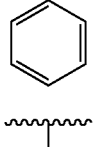 |
| 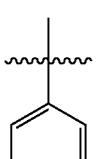 | 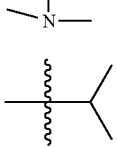 |

TABLE 1-continued
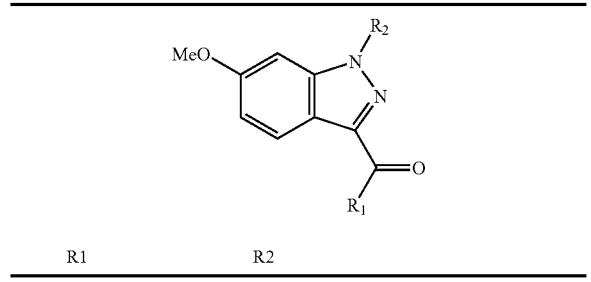
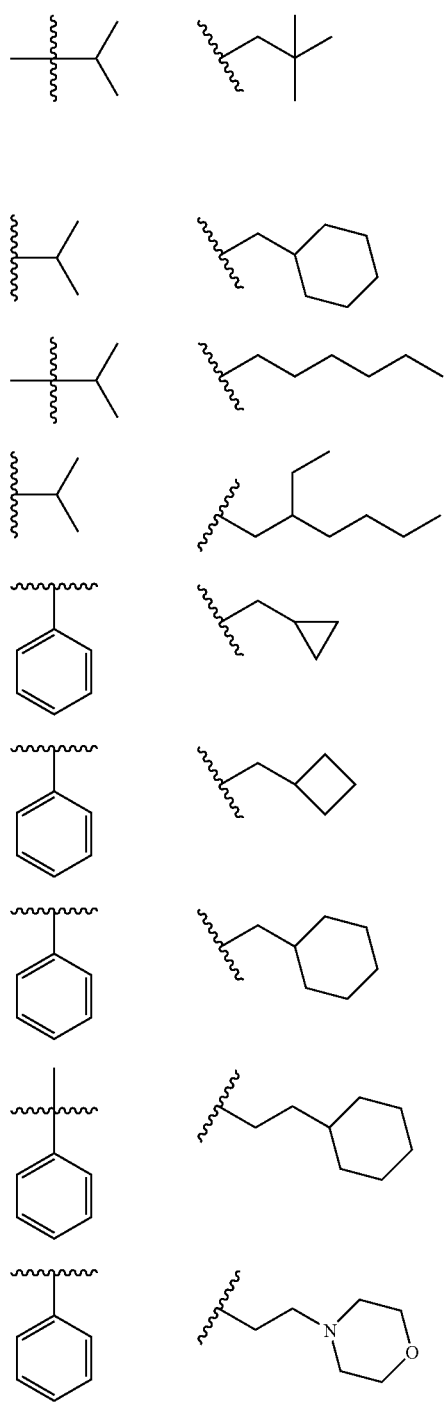
TABLE 1-continued
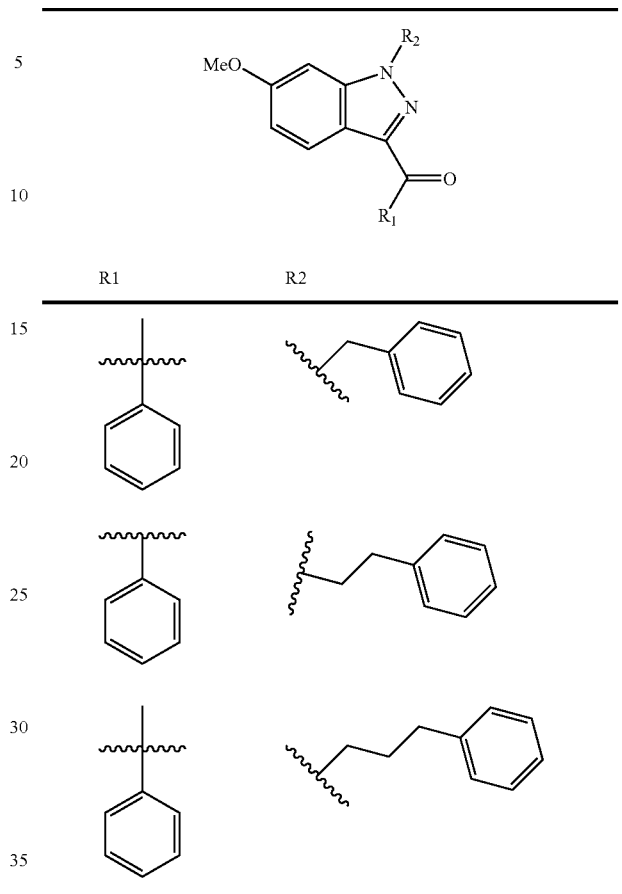
TABLE 2
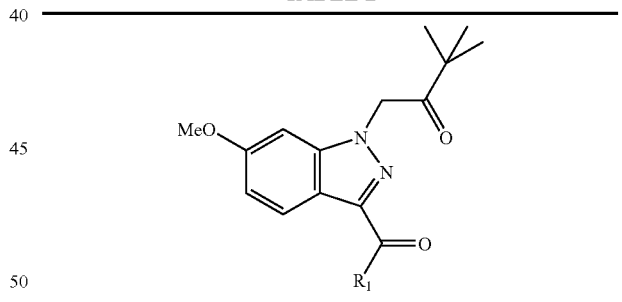
wherein R₁ is
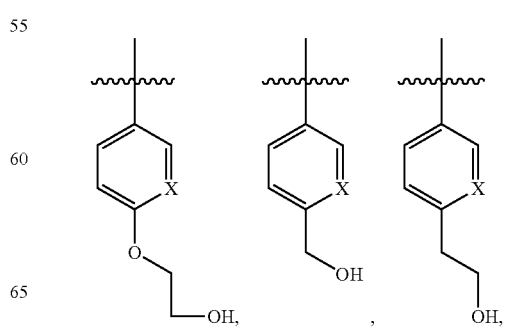

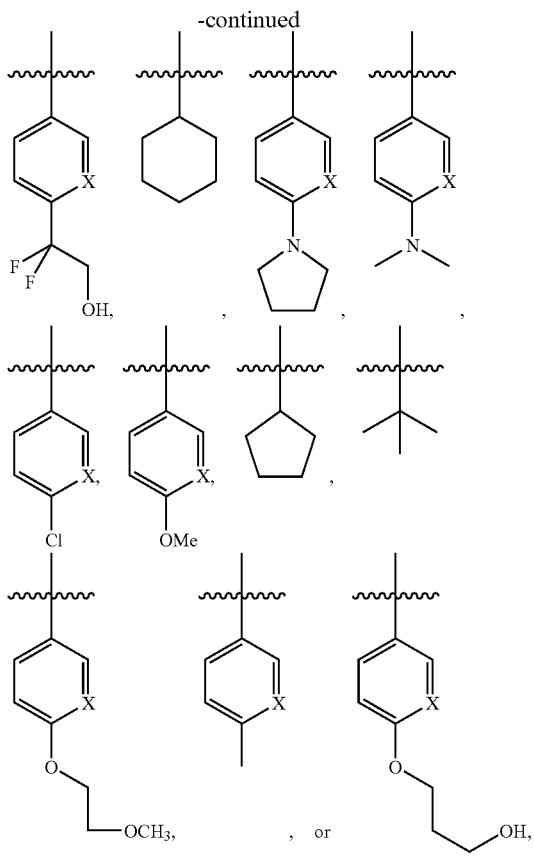

and X is N or CH;

or a pharmaceutically acceptable salt, enantiomer, diastereomer or mixture thereof.

The invention is described herein in detail using the terms defined below unless otherwise specified.

The compounds of the present invention may have asymmetric centers, chiral axes and chiral planes, and occur as racemates, racemic mixtures, and as individual diastereomers, with all possible isomers, including optical isomers, being included in the present invention. (See E. L. Eliel and S. H. Wilen *Stereochemistry of Carbon Compounds* (John Wiley and Sons, New York 1994), in particular pages 1119-1190)

When any variable (e.g. aryl, heterocycle, $R^1$, $R^6$ etc.) occurs more than one time in any constituent, its definition on each occurrence is independent at every other occurrence. Also, combinations of substituents/or variables are permissible only if such combinations result in stable compounds.

When $R^a$ is —O— and attached to a carbon it is referred to as a carbonyl group and when it is attached to a nitrogen (e.g., nitrogen atom on a pyridyl group) or sulfur atom it is referred to a N-oxide and sulfoxide group, respectively.

The term "alkyl" refers to a monovalent alkane (hydrocarbon) derived radical containing from 1 to 10 carbon atoms unless otherwise defined. It may be straight, branched or cyclic. Preferred alkyl groups include methyl, ethyl, propyl, isopropyl, butyl, t-butyl, cyclopropyl cyclopentyl and cyclohexyl. When the alkyl group is said to be substituted with an alkyl group, this is used interchangeably with "branched alkyl group".

Cycloalkyl is a specie of alkyl containing from 3 to 15 carbon atoms, unless otherwise defined, without alternating or resonating double bonds between carbon atoms. It may contain from 1 to 4 rings, which are fused. Examples of such cycloalkyl elements include, but are not limited to, cyclopropyl, cyclobutyl, cyclopentyl, cyclohexyl and cycloheptyl.

Alkenyl is $C_2$-$C_6$ alkenyl.

Alkoxy refers to an alkyl group of indicated number of carbon atoms attached through an oxygen bridge, with the alkyl group optionally substituted as described herein. Said groups are those groups of the designated length in either a straight or branched configuration and if two or more carbon atoms in length, they may include a double or a triple bond. Exemplary of such alkoxy groups are methoxy, ethoxy, propoxy, isopropoxy, butoxy, isobutoxy, tertiary butoxy, pentoxy, isopentoxy, hexoxy, isohexoxy allyloxy, propargyloxy, and the like.

Halogen (halo) refers to chlorine, fluorine, iodine or bromine.

Aryl refers to aromatic rings e.g., phenyl, substituted phenyl and the like, as well as rings which are fused, e.g., naphthyl, phenanthrenyl and the like. An aryl group thus contains at least one ring having at least 6 atoms, with up to five such rings being present, containing up to 22 atoms therein, with alternating (resonating) double bonds between adjacent carbon atoms or suitable heteroatoms. Examples of aryl groups are phenyl, naphthyl, tetrahydronaphthyl, indanyl, biphenyl, phenanthryl, anthryl or acenaphthyl and phenanthrenyl, preferably phenyl, naphthyl or phenanthrenyl. Aryl groups may likewise be substituted as defined. Preferred substituted aryls include phenyl and naphthyl.

The term heterocyclyl or heterocyclic, as used herein, represents a stable 3- to 7-membered monocyclic or stable 8- to 11-membered bicyclic heterocyclic ring which is either saturated or unsaturated, and which consists of carbon atoms and from one to four heteroatoms selected from the group consisting of N, O, and S, and including any bicyclic group in which any of the above-defined heterocyclic rings is fused to a benzene ring. The heterocyclic ring may be attached at any heteroatom or carbon atom which results in the creation of a stable structure. A fused heterocyclic ring system may include carbocyclic rings and need include only one heterocyclic ring. The term heterocycle or heterocyclic includes heteroaryl moieties. Examples of such heterocyclic elements include, but are not limited to, azepinyl, benzimidazolyl, benzisoxazolyl, benzofurazanyl, benzopyranyl, benzothiopyranyl, benzofuryl, benzothiazolyl, benzothienyl, benzoxazolyl, chromanyl, cinnolinyl, dihydrobenzofuryl, dihydrobenzothienyl, dihydrobenzothiopyranyl, dihydrobenzothiopyranyl sulfone, dihydropyrrolyl, 1,3-dioxolanyl, furyl, imidazolidinyl, imidazolinyl, imidazolyl, indolinyl, indolyl, isochromanyl, isoindolinyl, isoquinolinyl, isothiazolidinyl, isothiazolyl, isothiazolidinyl, morpholinyl, naphthyridinyl, oxadiazolyl, 2-oxoazepinyl, oxazolyl, 2-oxopiperazinyl, 2-oxopiperdinyl, 2-oxopyrrolidinyl, piperidyl, piperazinyl, pyridyl, pyrazinyl, pyrazolidinyl, pyrazolyl, pyridazinyl, pyrimidinyl, pyrrolidinyl, pyrrolyl, quinazolinyl, quinolinyl, quinoxalinyl, tetrahydrofuryl, tetrahydroisoquinolinyl, tetrahydroquinolinyl, thiamorpholinyl, thiamorpholinyl sulfoxide, thiazolyl, thiazolinyl, thienofuryl, thienothienyl, and thienyl. Preferably, heterocycle is selected from 2-azepinonyl, benzimidazolyl, 2-diazapinonyl, dihydroimidazolyl, dihydropyrrolyl imidazolyl, 2-imidazolidinonyl, indolyl, isoquinolinyl, morpholinyl, piperidyl, piperazinyl, pyridyl, pyrrolidinyl, 2-piperidinonyl, 2-pyrimidinonyl, 2-pyrollidinonyl, quinolinyl, tetrahydrofuryl, tetrahydroisoquinolinyl, and thienyl.

The term "heteroatom" means, O, S or N, selected on an independent basis.

The term "heteroaryl" refers to a monocyclic aromatic hydrocarbon group having 5 or 6 ring atoms, or a bicyclic aromatic group having 8 to 10 atoms, containing at least one heteroatom, O, S or N, in which a carbon or nitrogen atom is the point of attachment, and in which one or two additional carbon atoms is optionally replaced by a heteroatom selected from O or S, and in which from 1 to 3 additional carbon atoms are optionally replaced by nitrogen heteroatoms, said heteroaryl group being optionally substituted as described herein. Examples of such heterocyclic elements include, but are not limited to, benzimidazolyl, benzisoxazolyl, benzofurazanyl, benzopyranyl, benzothiopyranyl, benzofuryl, benzothiazolyl, benzothienyl, benzoxazolyl, chromanyl, cinnolinyl, dihydrobenzofuryl, dihydrobenzothienyl, dihydrobenzothiopyranyl, dihydrobenzothiopyranyl sulfone, furyl, imidazolyl, indolinyl, indolyl, isochromanyl, isoindolinyl, isoquinolinyl, isothiazolyl, naphthyridinyl, oxadiazolyl, pyridyl, pyrazinyl, pyrazolyl, pyridazinyl, pyrimidinyl, pyrrolyl, quinazolinyl, quinolinyl, quinoxalinyl, tetrahydroisoquinolinyl, tetrahydroquinolinyl, thiazolyl, thienofuryl, thienothienyl, thienyl and triazolyl. Additional nitrogen atoms may be present together with the first nitrogen and oxygen or sulfur, giving, e.g., thiadiazole.

This invention is also concerned with compositions and methods of treating ocular hypertension or glaucoma by administering to a patient in need thereof one of the compounds of formula I in combination with a β-adrenergic blocking agent such as timolol, betaxolol, levobetaxolol, carteolol, levobunolol, a parasympathomimetic agent such as epinephrine, iopidine, brimonidine, clonidine, para-aminoclonidine, carbonic anhydrase inhibitor such as dorzolamide, acetazolamide, metazolamide or brinzolamide, an EP4 agonist (such as those disclosed in WO 02/24647, WO 02/42268, EP 1114816, WO 01/46140 and WO 01/72268), a prostaglandin such as latanoprost, travaprost, unoprostone, rescula, S1033 (compounds set forth in U.S. Pat. Nos. 5,889,052; 5,296,504; 5,422,368; and 5,151,444); a hypotensive lipid such as lumigan and the compounds set forth in U.S. Pat. No. 5,352,708; a neuroprotectant disclosed in U.S. Pat. No. 4,690,931, particularly eliprodil and R-eliprodil as set forth in WO 94/13275, including memantine; or an agonist (if 5-HT2 receptors as set forth in PCT/US00/31247, particularly 1-(2-aminopropyl)-3-methyl-1H-imdazol-6-ol fumarate and 2-(3-chloro-6-methoxy-indazol-1-yl)-1-methyl-ethylamine. An example of a hypotensive lipid (the carboxylic acid group on the α-chain link of the basic prostaglandin structure is replaced with electrochemically neutral substituents) is that in which the carboxylic acid group is replaced with a $C_{1-6}$ alkoxy group such as $OCH_3$ ($PGF_{2\alpha}$ 1-$OCH_3$), or a hydroxy group ($PGF_{2\alpha}$ 1-OH).

Preferred potassium channel blockers are calcium activated potassium channel blockers. More preferred potassium channel blockers are high conductance, calcium activated potassium (Maxi-K) channel blockers. Maxi-K channels are a family of ion channels that are prevalent in neuronal, smooth muscle and epithelial tissues and which are gated by membrane potential and intracellular $Ca^{2+}$.

The present invention is based upon the finding that maxi-K channels, if blocked, inhibit aqueous humor production by inhibiting net solute and $H_2O$ efflux and therefore lower IOP. This finding suggests that maxi-K channel blockers are useful for treating other ophthamological dysfunctions such as macular edema and macular degeneration. It is known that lowering IOP promotes blood flow to the retina and optic nerve. Accordingly, the compounds of this invention are useful for treating macular edema and/or macular degeneration.

It is believed that maxi-K channel blockers which lower IOP are useful for providing a neuroprotective effect. They are also believed to be effective for increasing retinal and optic nerve head blood velocity and increasing retinal and optic nerve oxygen by lowering IOP, which when coupled together benefits optic nerve health. As a result, this invention further relates to a method for increasing retinal and optic nerve head blood velocity, increasing retinal and optic nerve oxygen tension as well as providing a neuroprotective effect or a combination thereof.

A number of marketed drugs function as potassium channel antagonists. The most important of these include the compounds Glyburide, Glipizide and Tolbutamide. These potassium channel antagonists are useful as antidiabetic agents. The compounds of this invention may be combined with one or more of these compounds to treat diabetes.

Potassium channel antagonists are also utilized as Class 3 antiarrhythmic agents mid to treat acute infarctions in humans. A number of naturally occurring toxins are known to block potassium channels including Apamin, Iberiotoxin, Charybdotoxin, Noxiustoxin, Kaliotoxin, Dendrotoxin(s), mast cell degranuating (MCD) peptide, and β-Bungarotoxin (β-BTX). The compounds of this, invention may be combined with one or more of these compounds to treat arrhythmias.

Depression is related to a decrease in neurotransmitter release. Current treatments of depression include blockers of neurotransmitter uptake, and inhibitors of enzymes involved in neurotransmitter degradation which act to prolong the lifetime of neurotransmitters.

Alzheimer's disease is also characterized by a diminished neurotransmitter release. Three classes of drugs are being investigated for the treatment of Alzheimer's disease cholinergic potentiators such as the anticholinesterase drugs (e.g., physostigmine (eserine), and Tacrine (tetrahydroaminocridine)); nootropics that affect neuron metabolism with little effect elsewhere (e.g. Piracetam, Oxiracetam; and those drugs that affect, brain vasculature such as a mixture of ergoloid mesylates and calcium channel blocking drugs including Nimodipine. Selegiline, a monoamine oxidase B inhibitor which increases brain dopamine and norepinephrine has reportedly caused mild improvement in some Alzheimer's patients. Aluminum chelating agents have been of interest to those who believe Alzheimer's disease is due to aluminum toxicity. Drugs that affect behavior, including neuroleptics, and anxiolytics have been employed. Anxiolytics, which are mild tranquilizers, are less effective than neuroleptics. The present invention is related to novel compounds which are useful as potassium channel antagonists.

The compounds within the scope of the present invention exhibit potassium channel antagonist activity and thus are useful in disorders associated with potassium channel malfunction. A number of cognitive disorders such as Alzheimer's Disease, memory loss or depression may benefit from enhanced release of neurotransmitters such as serotonin, dopamine or acetylcholine and the like. Blockage of Maxi-K channels maintains cellular depolarization and therefore enhances secretion of these vital neurotransmitters.

The compounds of this invention may be combined with anticholinesterase drugs such as physostigmine (eserine) and Tacrine (tetrahydroaminocridine), nootropics such as Piracetam, Oxiracetam, ergoloid mesylates, selective calcium channel blockers such as Nimodipine, or monoamine oxidase B inhibitors such as Selegiline, in the treatment of Alzheimer's disease. The compounds of this invention may also be combined with Apamin, Iberiotoxin, Charybdotoxin, Noxiustoxin, Kaliotoxin, Dendrotoxin(s), mast cell degranuating (MCD) peptide, β-Bungarotoxin (β-BTX) or a combination thereof in treating arrythmias. The compounds of this invention may further be combined with Glyburide, Glipizide, Tolbutamide or a combination thereof to treat diabetes.

The herein examples illustrate but do not limit the claimed invention. Each of the claimed compounds are potassium channel antagonists and are thus useful in the described neurological disorders in which it is desirable to maintain the cell in a depolarized state to achieve maximal neurotransmitter release. The compounds produced in the present invention are readily combined with suitable and known pharmaceutically acceptable excipients to produce compositions which may be administered to mammals, including humans, to achieve effective potassium channel blockage.

For use in medicine, the salts of the compounds of formula I will be pharmaceutically acceptable salts. Other salts may, however, be useful in the preparation of the compounds according to the invention or of their pharmaceutically acceptable salts. When the compounds of the present invention is acidic, suitable "pharmaceutically acceptable salts" refers to salts prepared from pharmaceutically acceptable non-toxic bases including inorganic bases and organic bases. Salts derived from inorganic bases include aluminum, ammonium, calcium, copper, ferric, ferrous, lithium, magnesium, manganic salts, manganous, potassium, sodium, zinc and the like. Particularly preferred are the ammonium, calcium, magnesium, potassium and sodium salts. Salts derived from pharmaceutically acceptable organic non-toxic bases include salts of primary, secondary and tertiary amines, substituted amines including naturally occurring substituted amines, cyclic amines and basic ion exchange resins, such as arginine, betaine caffeine, choline, $N,N^1$-dibenzylethylenediamine, diethylamin, 2-diethylaminoethanol, 2-dimethylaminoethanol, ethanolamine, ethylenediamine, N-ethylmorpholine, N-ethylpiperidine, glucamine, glucosamine, histidine, hydrabamine, isopropylamine, lysine, methylglucamine, morpholine, piperazine, piperidine, polyamine resins, procaine, purines, theobromine, triethylamine, trimethylamine tripropylamine, tromethamine and the like.

When the compound of the present invention is basic, salts may be prepared from pharmaceutically acceptable non-toxic acids, including inorganic and organic acids. Such acids include acetic, benzenesulfonic, benzoic, camphorsulfonic, citric, ethanesulfonic, fumaric, gluconic, glutamic, hydrobromic, hydrochloric, isethionic, lactic, maleic, malic, mandelic, methanesulfonic, mucic, nitric, pamoic, pantothenic, phosphoric, succinic, sulfuric, tartaric, p-toluenesulfonic acid and the like. Particularly preferred are citric, hydrobromic, hydrochloric, maleic, phosphoric, sulfuric and tartaric acids.

The preparation of the pharmaceutically acceptable salts described above and other typical pharmaceutically acceptable salts is more fully described by Berg et al., "Pharmaceutical Salts," *J. Pharm. Sci.*, 1977:66:1-19.

As used herein, the term "composition" is intended to encompass a product comprising the specified ingredients in the specific amounts, as well as any product which results, directly or indirectly, from combination of the specific ingredients in the specified amounts.

When a compound according to this invention is administered into a human subject, the daily dosage will normally be determined by the prescribing physician with the dosage generally varying according to the age, weight, sex and response of the individual patient, as well as the severity of the patient's symptoms.

The maxi-K channel blockers used can be administered in a therapeutically effective amount intravenously, subcutaneously, topically, transdermally, parenterally or any other method known to those skilled in the art.

Ophthalmic pharmaceutical compositions are preferably adapted for topical administration to the eye in the form of solutions, suspension, ointments, creams or as a solid insert. Ophthalmic formulations of this compound may contain from 0.001 ppm to 1% and especially 0.1 ppm to 1% of medicament. Higher dosages as for example, about 10% or lower dosages can be employed provided the dose is effective in reducing intraocular pressure, treating glaucoma, increasing blood flow velocity or oxygen tension. For a single dose, from between 0.01 to 5000 ng, preferably 0.1 to 500 ng, and especially 1 to 100 ng of the compound can be applied to the human eye.

The pharmaceutical preparation which contains the compound may be conveniently admixed with a non-toxic pharmaceutical organic carrier, or with a non-toxic pharmaceutical inorganic carrier. Typical of pharmaceutically acceptable carriers are, for example, water, mixtures of water and water-miscible solvents such as lower alkanols or aralkanols, vegetable oils, polyalkylene glycols, petroleum based jelly, ethyl cellulose, ethyl oleate, carboxymethyl-cellulose, polyvinylpyrrolidone, isopropyl myristate and other conventionally employed acceptable carriers. The pharmaceutical preparation may also contain non-toxic auxiliary substances such as emulsifying, preserving, wetting agents, bodying agents and the like, as for example, polyethylene glycols 200, 300, 400 and 600, carbowaxes 1,000, 1,500, 4,000, 6,000 and 10,000, antibacterial components such as quaternary ammonium compounds, phenylmercuric salts known to have cold sterilizing properties and which are non-injurious in use, thimerosal, methyl and propyl paraben, benzyl alcohol, phenyl ethanol, buffering ingredients such as sodium borate, sodium acetates, gluconate buffers, and other conventional ingredients such as sorbitan monolaurate, triethanolamine, oleate, polyoxyethylene sorbitan monopalmitylate, dioctyl sodium sulfosuccinate, monothioglycerol, thiosorbitol, ethylenediamine tetracetic acid, and the like. Additionally, suitable ophthalmic vehicles can be used as carrier media for the present purpose including conventional phosphate buffer vehicle systems, isotonic boric acid vehicles, isotonic sodium chloride vehicles, isotonic sodium borate vehicles and the like. The pharmaceutical preparation may also be in the form of a microparticle formulation. The pharmaceutical preparation may also be in the form of a solid insert. For example, one may use a solid water soluble polymer as the carrier for the medicament. The polymer used to form the insert may be any water soluble non-toxic polymer, for example, cellulose derivatives such as methylcellulose, sodium carboxymethyl cellulose, (hydroxyloweralkyl cellulose), hydroxyethyl cellulose, hydroxypropyl cellulose, hydroxypropylmethyl cellulose; acrylates such as polyacrylic acid salts, ethylacrylates, polyactylamides; natural products such as gelatin; alginates, pectins, tragacanth, karaya, chondrus, agar, acacia; the starch derivatives such as starch acetate, hydroxymethyl starch ethers, hydroxypropyl starch, as well as other synthetic derivatives such as polyvinyl alcohol, polyvinyl pyrrolidone, polyvinyl methyl ether, polyethylene oxide, neutralized carbopol and xanthan gum, gellan gum, and mixtures of said polymer.

Suitable subjects for the administration of the formulation of the present invention include primates, man and other animals, particularly man and domesticated animals such as cats and dogs.

The pharmaceutical preparation may contain non-toxic auxiliary substances such as antibacterial components which are non-injurious in use, for example, thimerosal, benzalkonium chloride, methyl and propyl paraben, benzyldodecinium bromide, benzyl alcohol, or phenylethanol; buffering ingredients such as sodium chloride, sodium borate, sodium acetate, sodium citrate, or gluconate buffers; and other conventional ingredients such as sorbitan monolaurate, triethanolamine, polyoxyethylene sorbitan monopalmitylate, ethylenediamine tetraacetic acid, and the like.

The ophthalmic solution or suspension may be administered as often as necessary to maintain an acceptable IOP level in the eye. It is contemplated that administration to the mammalian eye will be about once or twice daily.

For topical ocular administration the novel formulations of this invention may take the form of solutions, gels, ointments, suspensions or solid inserts, formulated so that a unit dosage comprises a therapeutically effective amount of the active component or some multiple thereof in the case of a combination therapy.

The following examples given by way of illustration is demonstrative of the present invention.

Definitions of the terms used in the examples are as follows:

SM—Starting material,

DMSO—dimethyl sulfoxide,

TLC—thin layer chromatography,

SGC—silica gel chromatography,

PhMgBr—phenylmagnesiumbromide h=hr=hour.

THF—tetrahydrofuran,

DMF—dimethylformamide, min—minute,

LC/MS—liquid chromatography/mass spectrometry,

HPLC—high performance liquid chromatography,

DBOP—Benzotriazol-1-yloxytris-(dimethyl amino)phosphonium hexafluorophosphate, equiv=eq=equivalent, NBS—N-Bromosuccinamide and AIBN-2,2'-azobisisobutyronitrile.

The compounds of this invention can be made, with modification where appropriate, in accordance with Schemes 1 through 4. Examples 1-3 are also produced in accordance with Schemes 1 and/or 2.

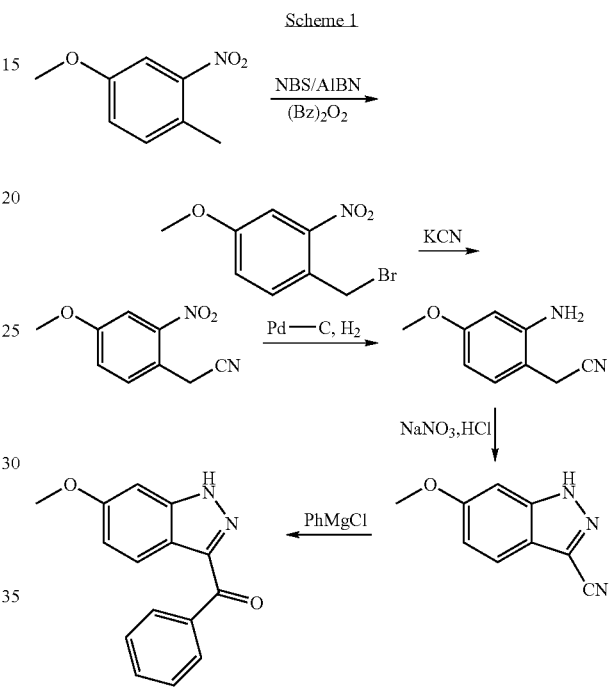

Scheme 1

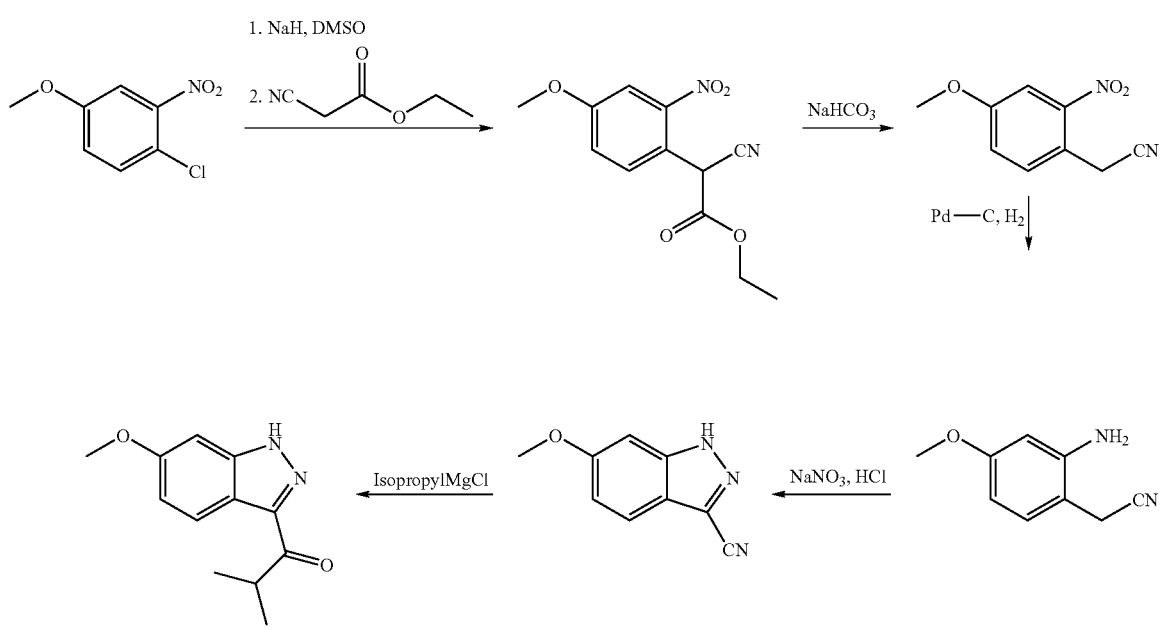

Scheme 2

In Schemes 1 and 2 nitroanisole is brominated rising NBS, AIBN and benzoyl peroxide. Treatment of the bromonitroanisole with potassium cyanide yielded the cyanonitroanisole. Conversion of the nitro group to an amine is accomplished by hydrogenation. The amine is then treated with sodium nitrite and HCl to yield the indazole ring. In this reaction as soon as the diazonium is generated by nitrosation of the aniline moiety it is trapped intramolecularily by the acidic benzyl cyanide. Tautomerization of the resultant derivative gives the indazole nucleus. Treatment of the nitrile with a Gringard followed by hydrolysis of the vesnltant imino-magnesium complex gives the desired alkyl/aryl ketone.

Scheme 3

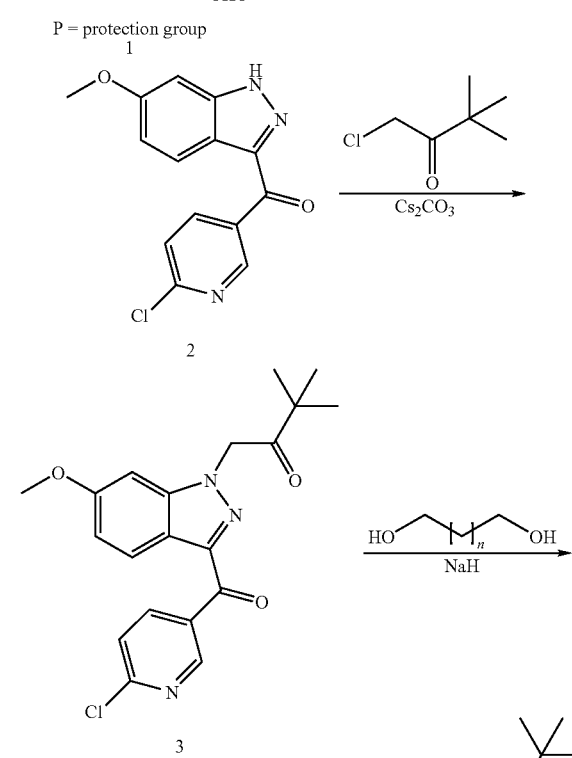

Scheme 4

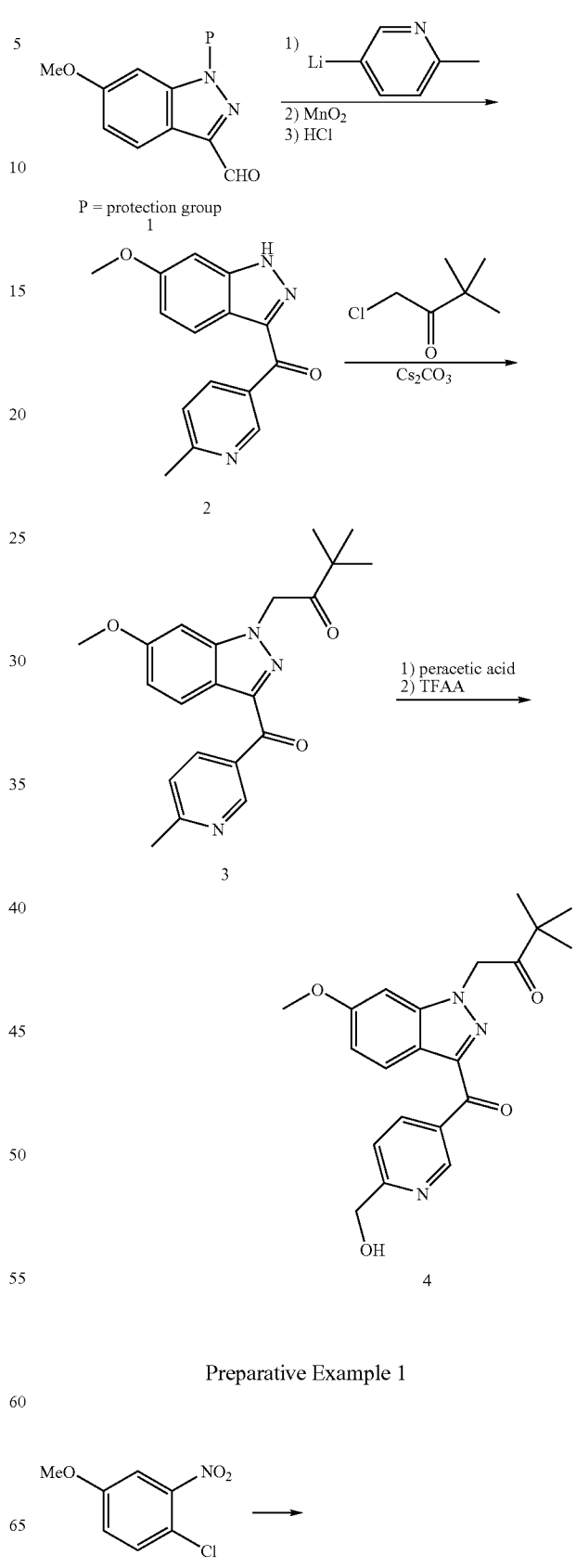

Preparative Example 1

-continued

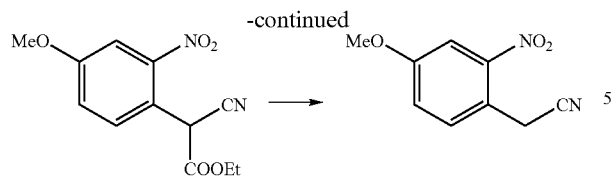

In a 500 mL flask was charged 336 mmoles (13.44 g; 60%) of NaH. Under argon 150 mL of DMSO was added, followed by dropwise addition of 32 mL of ethyl cyanoacetate (2.2 equiv.; 352 mmoles) at 5° C. After al the addition the reaction was warmed upto room temperature over 1 h. 30 g of starting nitro benzene derivative was added (160 mmoles) as a powder. The reaction mixture was heated in a closed system at 90° C. for 8 hours. Acidification and standard work-up gave a crude oily residue which was purified over a silica-gel column to give 39 g of desired crystalline product which was decarboxylated to give the benzyl nitrile as follows. Thirty eight grams of SM obtained above was dissolved ins 400 mL or 1N sodium carbonate. The homogenous solution was stirred at rt for two days. TLC analysis indicated completion of reaction. The reaction mixture was acidified and extracted with ethyl acetate (100 mL×4). The combined organic phases was dried over sodium sulphate and concentrated and residue was subjected to SGC to give the desired product.

1H NMR CDCL3: 7.72 (1H, d, J=3 Hz); 7.61 (1H, d, J=8.5 Hz); 7.25 (1H, dd, J=3 and 8.5 Hz); 4.17 (2H, s); 3.94 (3H, s). LCMS [M+H]=193.

Preparative Example 2

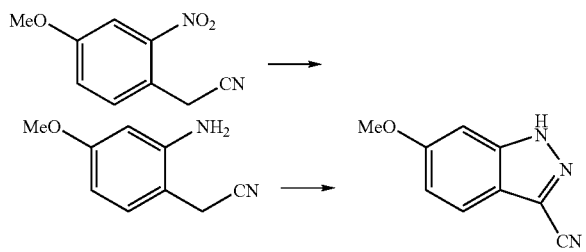

10 g of benzylnitrile derivative was dissolved in THF 20 mL followed by dilution with 50 mL of methanol. The reaction mixture was taken in a pressure tube, Pd—C (10% wt/10 mole %) was added and the reaction mixture was hydrogenated at 40 psi. After the requisite amount of hydrogen for the reduction of the $NO_2$ group was consumed the reaction was stopped. TLC analysis indicated a spot to spot conversion. The reaction mixture was filtered over a pad of celite and the filtrate was concentrated to a solid and used in the next step directly. Crude aniline derivative (52 mmoles was dissolved/suspended in 2N HCl (150 mL), cooled to 5° C. followed by the addition of 5.4 g of sodium nitrite in 10 mL of water. The reaction mixture was allowed to stir for 1 h with gradual warming to room temperature. TLC analysis indicated complete consumption of SM and the formation of a new spot. The reaction mixture was extracted with ethyl acetate (100 mL×4); organic phase was collected, dried and concentrated. The residue was purified by SGC to give desired product. LCMS [M+H]=174

Preparative Example 3

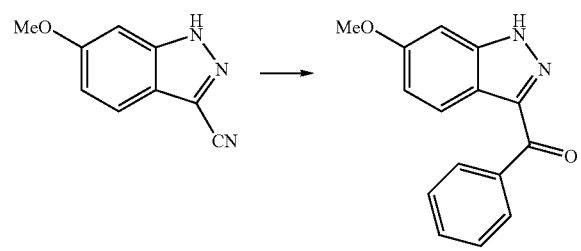

Nitrile (1.5 g) obtained from Preparative Example 2 was dissolved in 20 mL of dry THF and under argon 3 equiv. of PhMgBr (1M in THF) was added at 5° C. The reaction mixture was stirred at room temperature for 1 h. The reaction was carefully quenched by addition of water and 1N HCl (15 ml). The quenched reaction mixture was stirred at room temperature for 1 hour then extracted with ethyl acetate (20 mL×3); combined organic phases were dried over sodium sulfate and concentrated to a solid residue which was azeotroped with toluene three times.

LCMS [M+H]=253

Preparative Example 4

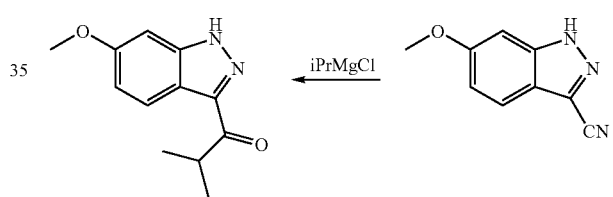

Weighed out 4.15 g of indazole and azeoptroped water with 2 toluene (100 ml) washings, pulling off toluene azeotrope by rotovap. Dried thoroughly under high vacuum and performed argon purges. Dissolved in 40 ml dry THF and 92 ml dry ether under argon. Cooled to 5° C. in ice water bath. Charged 3 eq of isopropylmagnesium chloride ((6 ml of a 2M solution in THF) and stirred for 0.5 hr at room temp. Carefully charged 1N HCl (240 ml) and stirred for 1 h. Monitored reaction by TLC. Extracted with EtOAc, rotovaped and produced desired product.

LCMS [M+H]=219

Preparative Example 5

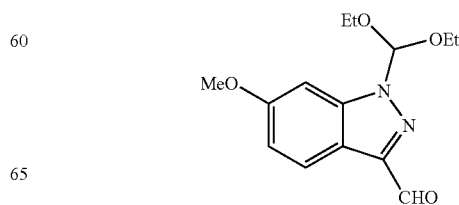

Step A:

100 g of 2-fluoro-4-methoxy-acetophenone in 400 mL of ethylene glycol was stirred at room temperature with hydrazine (0.624 mol, 20 g) for 4 h after which the reaction mixture was heated to 150° C. for 48 h. TLC analysis indicated complete reaction. Partitioned the reaction mixture into dichloromethane and brine. Dried organic phase over sodium sulphate and evaporated to a solid. Re-crystallized from hexane/dicholomethane gave 6-methoxy-3-methyl-1H-indazole.

1H NMR (CDCL3): 7.5 (1H, d, 7.5 Hz); 6.8 (2H, m); 3.8 (3H, s); 2.55 (3H, s)

LCMS [M+H]=163

100 g of BOC-protected indazole was dissolved in 600 mL of CCl4, followed by addition of 1.1 equiv of NBS and 0.2 equiv of Bz2O. Reaction mix was vac-purged with argon and set to reflux for 5 h in presence of light from a sun lamp. Reaction mixture was filtered over a pad of SG and concentrated. Residual oil was purified over a short SGC. Monobromide and mixed fractions of di-bromo derivative were obtained.

mono-bromide: 1H NMR (CDCL3): 7.7 (1H, d, 7.5 Hz); 7.6 (1H, bs); 6.95 (1H, dd); 4.7 (2H, s); 3.9 (3H, s); 1.7 (9H, s);

di-bromide: 1H NMR (CDCL3): 8.05 (1H, d, J=7.5 Hz); 7.6 (1H, bs); 7.0 (1H, dd); 6.85 (1H, s); 3.9 (3H, s); 1.7 (9H, s);

78 g of 6-methoxy-3-methyl-1H-indazole was dissolved in 1 L of MeCN containing 111 equiv of tri-ethyl amine, 0.2 equiv of DMAP was cooled to −5° C.; followed by slow addition of Boc$_2$O (1.1 equiv) in 200 mL of MeCN. After 2 h of stirring the reaction at room temperature the reaction mixture was evaporated to an oil which was partitioned between EtOAc and brine, dried over sodium sulphate and evaporated. The residue was applied to a short SGC and eluted with 15% EtOAc in hexane. Evaporation gave Boc-protected product.

1H NMR (CDCL3): 7.6 (1H, bs); 7.42 (1H, d, J=7.5 Hz); 6.85 (1H, dd); 3.8 (3H, s); 2.5 (3H, s); 1.7 (9H, s)

LCMS [M+H]=263

To a solution of dibromide (23.2 g) in acetic acid was added sodium acetate (22.5 g). The mixture was placed in oil bath and refluxed for a couple of hours until reaction completed. The mixture was cooled to room temperature and then poured into ice/water to give desired compound as an off-white solid. The solid was isolated by filtration and dried over nitrogen atmosphere.

$^1$H NMR (CDCl$_3$): δ 10.23 (1H, s); 8.19 (1H, d); 7.02 (1H, dd); 6.96 (1H, d); 3.90 (3H, s).

Step B:

To the intermediate from Step A was added triethyl orthoformate (40 ml) and heated to 130° C. for a couple of hours. The resulting mixture was concentrated to dry to give title compound as a brown solid.

$^1$H NMR (DMSO): δ 10.08 (1H, s); 7.98 (1H, d); 7.25 (1H, d); 7.02 (1H, dd); 6.81 (1H, s); 3.82 (3H, s); 3.52 (4H, q); 1.11 (6H, t).

Preparative Example 6

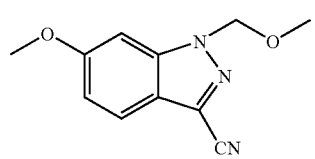

Oil free NaH (120 mg, 60% NaH in mineral oil was washed with hexanes 3 times.) suspended in DMF was added intermediate from Preparative Example 2 (346 mg) at RT. After bubbles subsided, the mixture was stirred at RT for 30 min and MOM—Cl (0.23 ml) was added. After the reaction completed, the mixture was poured into ice/water to give compound as a solid. The crude material was purified by silica gel (hexanes/ethyl acetate=3/1) to give title compound.

$^1$H NMR (CDCl$_3$): 7.72 (1H, d); 7.06 (1H, dd); 6.99 (1H, d); 5.72 (2H, s); 3.94 (3H, s); 3.36 (3H, s).

Preparative Example 7

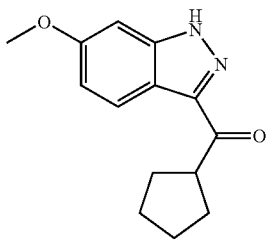

To a solution of intermediate from preparative Example 2 (1.00 g, 5.75 mmol) dissolved in THF (15 mL) was added cyclopentyl magnesium bromide (6.32 mL, 12.65 mmol) at 0° C. The reaction was allowed to warm to ambient temperature and was quenched with saturated NH$_4$Cl upon completion. The resulting reaction mixture was extracted with EtOAc and the combined organic layers were washed with brine, dried over MgSO$_4$, and concentrated in vacuo. The product was purified via SiO$_2$ gel chromatography to yield 580 mg of the desired product. $^1$H NMR (CDCl$_3$) δ: 1.702 (2H, m), 1.803 (2H, m), 2.005 (4H, m), 3.904 (3H, s), 4.070 (1H, m), 6.915 (1H, s), 7.010 (1H, d), 8.272 (1H, d).

Preparative Example 8

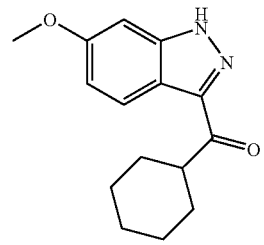

The desired compound was prepared by a procedure similar to the one described for Preparative Example 7, but cyclohexyl magnesium bromide was used in place of cyclopentyl magnesium bromide. $^1$H NMR (CDCl$_3$) δ: 1.321 (1H, m), 1.479 (2H, m), 1.604 (2H, m), 1.781 (1H, m), 1.861 (2H, m), 2.000 (2H, m), 3.641 (1H, m), 3.902 (3H, s), 6.923 (1H, s), 7.008 (1H, d), 8.259 (1H, d).

Example 1

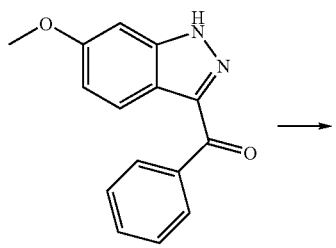

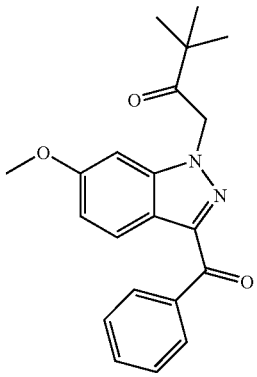

Indazole (0.55 mmoles from Preparative Example 3) starting material obtained as above was dissolved in DMF (3 mL) followed by the addition of sodium hydride (0.88 mmoles). The reaction was stirred at room temperature for 15 min, followed by the addition of 1-bromo-pinacolone (0.669 mmoles). The reaction was stirred at room temperature for 30 min. TLC and LC-MS analysis indicated complete consumption of starting material concurrent with the formation of a new product spot. The reaction mixture was quenched by the addition of water. Standard aqueous work-up followed by purification of crude by SGC gave the desired product as white solid.

1H NMR CDCL3: 8.3 (3H, m); 7.61 (1H, t, J=7.5 Hz); 7.52 (2H, dd, J=7.5 and 7.0 Hz); 7.04 (1H, dd, J=2 and 9 Hz); 6.56 (1H, d, J=2 Hz); 5.4 (2H, s); 3.94 (3H, s); 1.4 (9H, s). LCMS [M+H]=351.

Example 2

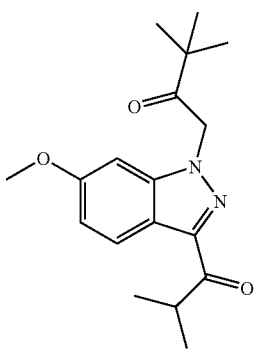

Indazole (0.60 mmoles from Preparative Example 4) starting material obtained as above was dissolved in DMF (3 mL) followed by the addition of sodium-hydride (0.88 mmoles). The reaction was stirred at room temperature for 15 min, followed by the addition of 1-bromo-pinacolone (0.669 mmoles). The reaction was stirred at room temperature for 30 min. TLC and LC-MS analysis indicated complete consumption of starting material concurrent with the formation of a new product spot. The reaction mixture was quenched by the addition of water. Standard aqueous work-up followed by purification of crude by SGC gave the desired product as white solid.

1H NMR in CDCL: 8.22 (1H, d, J=9 Hz); 6.97 (1H, dd, J=2 and 9 Hz); 6.5 (1H, d J=2 Hz); 5.4 (2H, s); 3.94 (3H, s); 2.8 (1H, m); 1.38 (9H, s); 1.27 (6H, d, J=6.5 Hz).

LCMS=[M+H]=317

Example 3

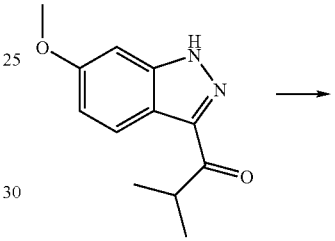

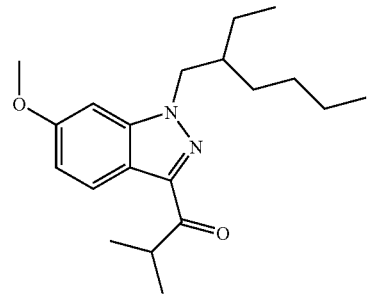

133 mg of indazole from Preparative Example 4 was dissolved in dry DMF (3 mL), followed by the addition of sodium hydride (24.3 mg, 60% oil dispersion). After stirring at room temperature for 15 min. 0.2 mL of 2-ethyl-hexyl iodide was added. The reaction mixture was allowed to stir for an additional 10 h. Upon standard aqueous work-up followed by purification by SGC the desired product was obtained.

1HNMR CDCL3: 8.22 (1H, d, J=8.5 Hz); 7.0 (1H, dd, J=8.5 and 2 Hz); 6.75 (1H, d, J=2 Hz); 4.23 (2H, d, J=7.5 Hz); 3.9 (3H, s); 2.2 (1H, m); 0.8-1.5 (15h, m).

LCMS [M+H]=331

Examples 4 through 15 as shown below are made, with some modification of the desired compound of Example 3, by alkylation of the indazole as described in Example 1. Additionally, analogs of Examples 1 and 4-15 can be prepared following analogous procedures using the indazole of Preparative Example 4 or alternatively another indazole prepared following procedures described herein.

Example 4

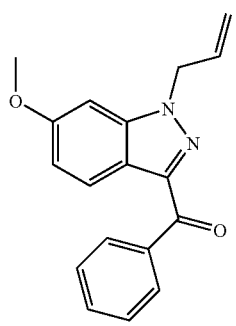

1H NMR CDCL3: 8.35 (3H, m); 7.6 (1H, t); 7.55 (2H, t); 7.1 (1H, dd, J=8.5 and 2 Hz); 6.8 (1H, d, J=2 Hz); 5.9 (1H, m); 5.15 (2H, m); 4.5 (2H, t); 3.9 (3H, s); 2.8 (2H, m).
LCMS [M+H]=307

Example 5

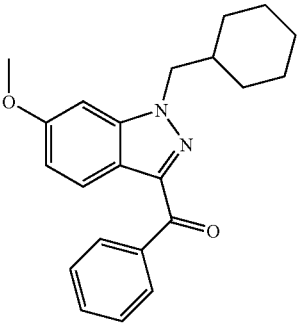

1H NMR CDCL3: 8.35 (3H, m); 7.6 (1H, t); 7.55 (2H, t); 7.1 (1H, dd, J=8.5 and 2 Hz); 6.8 (1H, d, J=2 Hz); 4.25 (2H, d, J=7.5 Hz); 3.9 (3H, s); 1-2.2 (11H, m).
LCMS [M+H]=349

Example 6

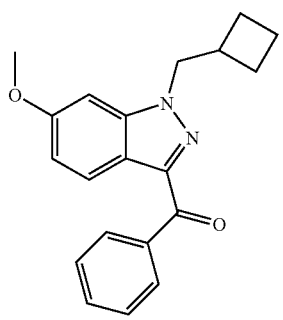

1H NMR CDCL3: 8.35 (3H, m); 7.6 (1H, t); 7.55 (2H, t); 7.1 (1H, dd, J=8.5 and 2 Hz); 6.8 (1H, d, J=2 Hz); 4.45 (2H, d, J=7.5 Hz); 3.9 (3H, s); 3.0 (1H, m); 1.8-2.2 (6H, m).
LCMS [M+H]=321

Example 7

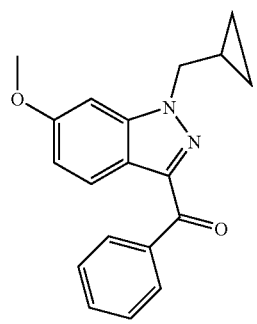

1H NMR CDCL3: 8.35 (3H, m); 7.6 (1H, t); 7.55 (2H, t); 7.1 (1H, dd, J=8.5 and 2 Hz); 6.8 (1H, d, J=2 Hz); 4.35 (2H, d, J=7.5 Hz); 3.9 (3H, s); 1.4 (1H, m); 0.7 (2H, m); 0.5 (2H, m).
LCMS [M+H]=307

Example 8

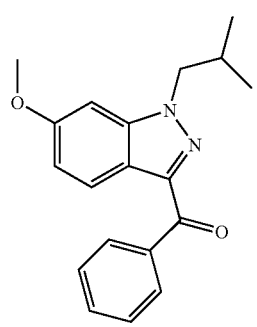

1H NMR CDCL3: 8.35 (3H, m); 7.6 (1H, t); 7.55 (2H, t); 7.1 (1H, dd, J=8.5 and 2 Hz); 6.8 (1H, d, J=2 Hz); 4.2 (3H, s); 3.9 (3H, s); 1.1 (9H, s).
LCMS [M+H]=323

Example 9

1H NMR CDCL3: 8.35 (3H, m); 7.6 (1H, t); 7.55 (2H, t); 7.1 (1H, dd, J=8.5 and 2 Hz); 6.8 (1H, d, J=2 Hz); 4.25 (2H, d, J=7.5 hZ); 3.9 (3H, s); 2.6 (1H, m); 1.02 (6H, d).
LCMS [M+H]=309

Example 10

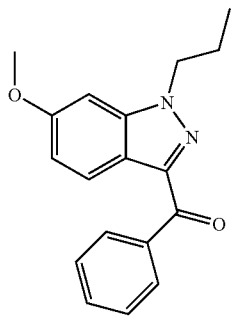

1H NMR CDCL3: 8.35 (3H, m); 7.6 (1H, t); 7.55 (2H, t); 7.1 (1H, dd, J=8.5 and 2 Hz); 6.8 (1H, d, J=2 Hz); 4.4 (2H, t, J=7.5 Hz); 3.9 (3H, s); 2.o (2H, m); 1.02 (3H, t, J=7.5 Hz).
LCMS [M+H]=295

Example 11

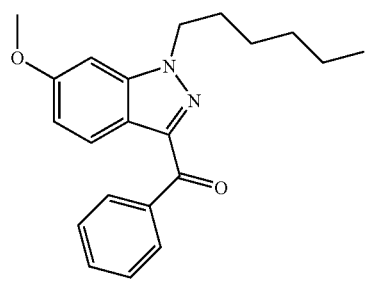

1H NMR CDCL3: 8.35 (3H, m); 7.6 (1H, t); 7.55 (2H, t); 7.1 (1H, dd, J=8.5 and 2 Hz); 6.8 (1H, d, J=2 Hz); 4.4 (2H, t, J=7.5 Hz); 3.9 (3H, s); 2.0 (2H, m); 0.8-1.5 (5H, m).
LCMS [M+H]=337

Example 12

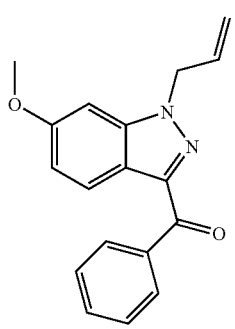

1H NMR CDCL3: 8.35 (3H, m); 7.6 (1H, t); 7.55 (2H, t); 7.1 (1H, dd, J=8.5 and 2 Hz); 6.8 (1H, d, J=2 Hz); 6.2 (1H, m); 5.0-5.4 (3H, m); 3.9 (3H, s).
LCMS [M+H]=293

Example 13

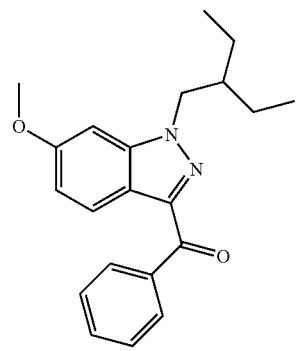

1H NMR CDCL3: 8.35 (3H, m); 7.6 (1H, t); 7.55 (2H, t); 7.1 (1H, dd, J=8.5 and 2 Hz); 6.8 (1H, d, J=2 Hz); 4.4 (2H, d, J=7.5 Hz); 3.9 (3H, s); 2.1 (1H, m); 1.4 (4H, m); 1.0 (6H, t, J=7.5 Hz).
LCMS [M+H]=337

Example 14

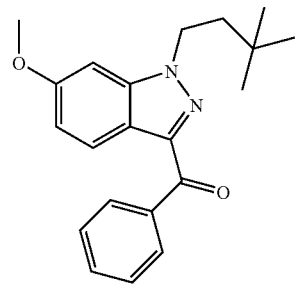

1H NMR CDCL3: 8.35 (3H, m); 7.6 (1H, t); 7.55 (2H, t); 7.1 (1H, dd, J=8.5 and 2 Hz); 6.8 (1H, d, J=2 Hz); 4.4 (2H, t, J=7.5 Hz); 3.9 (3H, s); 1.9 (2H, t, J=7.5 Hz); 1.1 (9H, s).
LCMS [M+H]=337.

Example 15

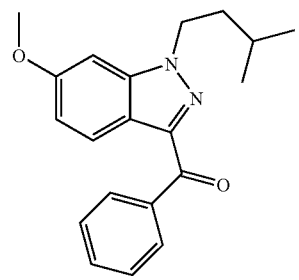

1H NMR CDCL3: 8.35 (3H, m); 7.6 (1H, t); 7.55 (2H, t); 7.1 (1H, dd, J=8.5 and 2 Hz); 6.8 (1H, d, J=2 Hz); 4.5 (2H, t, J=7.5 Hz); 3.9 (3H, s); 1.9 (2H, m); 1.7 (1H, m); 1.05 (6H, d, J=7.5 Hz).

LCMS [M+H]=323

Example 16

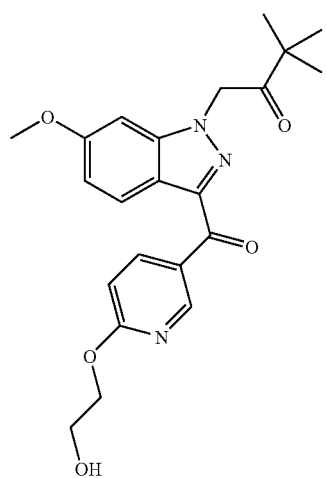

Step A:

To a solution of 5-iodo-2-chloropyridine (2.56 g, 10.78 mmol) in THF (10 mL) was added iPrMgBr dropwise at −78° C. The reaction stirred for 1 h before Preparative Example 5 (1.17 g, 6.10 mmol) was added as a solution in THF (5 mL). After 2 h and the reaction was quenched with 1N NaOH and extracted with EtOAc. The combined organic layers were washed with brine, dried over MgSO$_4$, and concentrated in vacuo. To a solution of the crude product in toluene (50 mL) was added MnO$_2$ (2.173 g, 25.0 mmol) and the reaction mixture was heated to 130° C. After 1 h the reaction was complete, filtered through a celite pad, and concentrated in vacuo. The crude product was dissolved in THF (16 mL) and 4 mL of 1N HCl was added dropwise. The reaction stirred at RT until TLC analysis indicated completion. The reaction mixture was cooled to 0° C. and the solid precipitate was collected. $^1$H NMR (CD$_3$OD) δ: 3.900 (3H, s), 7.013 (1H, d), 7.062 (1H, s), 7.627 (1H, d), 8.672 (1H, d), 9.306 (1H, s).

Step B:

To a solution of the intermediate from Step A (1.00 g, 3.48 mmol) and Cs$_2$CO$_3$ (3.396 g, 10.45 mmol) in DMF (14 mL) was added 1-chloropinacolone (0.681 mL, 5.22 mmol). After 40 min the reaction was complete and quenched with H$_2$O. The reaction mixture was extracted with EtOAc and the combined organic layers were washed with H$_2$O, brine dried over MgSO$_4$, and concentrated in vacuo to yield the desired product. $^1$H NMR (CD$_3$OD) δ: 1.344 (9H, s), 3.888 (3H, s), 6.947 (1H, s), 7.043 (1H, d), 7.625 (1H, d), 8.221 (1H, d), 8.624 (1H, d), 9.257 (1H, d).

Step C:

40.6 mg (1.036 mmol) of NaH (60% dispersion in mineral oil) was washed 3× with hexane and dried under nitrogen. Ethylene glycol (1 mL) was added to the dry NaH and the reaction stirred for 20 min at 60° C. To the reaction mixture was added the intermediate from Step B (100 mg, 0.259 mmol) as a solution in THF (1.5 mL). The reaction continued to stir overnight at 60° C. Upon completion, the THF was removed in vacuo, diluted with EtOAc, washed with H$_2$O, brine, dried over MgSO$_4$, and concentrated in vacuo. The crude residue was purified via silica gel chromatography.

1.376 (9H, s), 3.889 (3H, s), 4.021 (2H, m), 4.608 (2H, m), 5.429 (2H, s), 6.543 (1H, s), 6.223 (1H, d), 7.054 (1H, d), 8.336 (1H, d), 8.541 (1H, d), 9.310 (1H, s).

Example 17

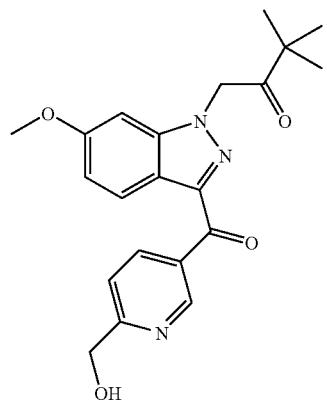

Step A:

To a solution of 5-bromo-2-methylpyridine (736 mg, 4.31 mmol) in THF (15 mL) was added nBuLi dropwise (2.156 mL, 5.39 mmol, 2.5 M in hexanes) at −78° C. The reaction stirred for 1 h before Preparative Example 5 (1.00 g, 3.59 mmol) was added as a solution in THF (5 mL). The starting material was consumed after 2 h and the reaction was quenched with 1N NaOH and extracted with EtOAc. The combined organic layers were washed with brine, dried over MgSO$_4$, and concentrated in vacuo. A solution of the crude product in toluene (20 mL) was added MnO$_2$ (0.414 g, 4.77 mmol) and the reaction mixture was heated to 130° C. After 1 h the reaction was complete, filtered through a celite pad, and concentrated in vacuo. The crude product was dissolved in THF and 4 mL of 1N HCl was added dropwise. After 1 h reaction mixture was cooled to 0° C. and the solid precipitate was collected. $^1$H NMR (DMSO) δ: 2.553 (3H, s), 3.832 (3H, s), 7.000 (1H, d), 7.089 (1H, s), 7.451 (1H, d), 8.100 (1H, d), 8.430 (1H, d), 9.220 (1H, s).

Step B:

This compound was made as described in Step B of Example 16.

$^1$H NMR (CDCl$_3$) δ: 1.38 (9H, s), 2.65 (3H, s), 3.85 (3H, s), 5.22 (2H, s), 6.56 (1H, s), 7.05 (1H, d), 7.32 (1H, d), 8.34 (1H, d), 8.45 (1H, d), 9.50 (1H, s).

Step C:

To a stirring solution of the intermediate from Step B (74 mg, 0.202 mmol) in CH$_2$Cl$_2$ was added MCPBA (67 mg, 0.303 mmol) at 0° C. TLC indicated the reaction was complete after 1.5 h and the reaction mixture was concentrated in vacuo. The crude residue was dissolved in EtOAc and washed with saturated sodium bisulfite, H$_2$O, brine, dried over MgSO₄, and concentrated in vacuo. Purified via silica gel chromatography. The N-oxide was dissolved in CH₂Cl₂ and TFAA was added dropwise at 0° C. After 2 h the reaction was concentrated in vacuo and purified via silica gel chromatography.

¹H NMR (CDCl₃) δ: 1.373 (9H, s), 3.898 (3H, s), 4.882 (2H, s), 5.428 (2H, s), 6.564 (1H, s), 7.066 (1H, d), 7.429 (1H, d), 8.352 (1H, d), 8.581 (1H, d), 9.541 (1H, s).

Example 18

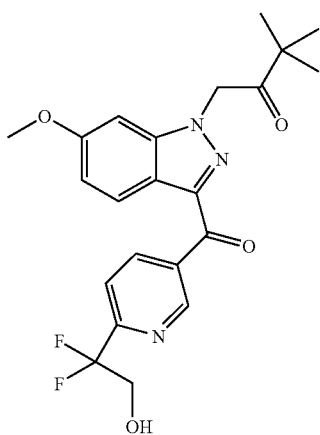

Step A:

To a solution of 2-pyridineacetic acid, 5-bromo-α,α-difluoro-, ethyl ester (13.4 g; prepared according to "Ero, H.; Haneko, Y.; Sakamoto, T. *Chem Pharm. Bull.* 2000, 48, 982.") in ethanol was added sodium borohydride (2.3 g) portion-wise at 0° C. After stirring at 0° C. for 1 hour, the mixture was poured into water and extracted with ethyl acetate. The organic layer was washed with 1N NaOH$_{aq}$, brine, dried (MgSO₄), and concentrated under reduced pressure to afford crude alcohol. The crude alcohol in methylene chloride was added imidazole (4.1 g) and TBS—Cl (8.3 g) at 0° C. The mixture was stirred for 1 hour. The reaction was poured into 0.1 N HCl$_{aq}$ extracted with methylene chloride. The organic layer was washed with brine, dried (MgSO₄) and evaporated. The residue was purified by silica gel (100% methylene chloride) to give desired compound as a colorless oil.

¹H NMR (CDCl₃): δ 8.75 (1H, d); 7.95 (1H, dd); 7.57 (1H, d); 4.20 (2H, t); 0.82 (9H, s); 0.02 (6H, s).

Step B:

The desired compound was prepared by a procedure similar to the one described for Example 16, Step A.

¹H NMR (DMSO): δ 9.35 (1H, d); 8.65 (1H, dd); 8.14 (1H, d); 7.88 (1H, d); 7.10 (1H, d); 7.03 (1H, dd); 4.05 (2H, t); 3.85 (3H, s).

LC-MS (M+H)=334.2.

Step C:

The desired compound vas prepared by a procedure similar to the one described for Example 16, Step B. This compound was purified by silica gel (hexanes/ethyl acetate=1/1) and crystallized from hexanes/ethyl acetate.

¹H NMR (CHCl₃): δ 9.53 (1H, d); 8.71 (1H, dd); 8.35 (1H, d); 7.88 (1H, d); 7.08 (1H, dd); 6.57 (1H); 5.44 (2H, s); 4.32 (2H, t); 3.91 (3H, s); 1.38 (9H, s).

LC-MS (M+H)=432.3.

Example 19

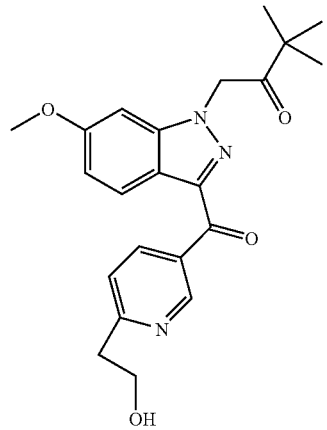

Step A:

To a solution of 2,5-dibromopyridine (2.4 g) in toluene was added tributylallyltin (3.4 ml) and dichlorobis(triphenylphosphine)palladium (0.7 g) under nitrogen atmosphere. The mixture was refluxed for a couple of hours and concentrated under reduced pressure. The residue was re-dissolved in "wet ether" and added DBU (3 ml) slowly to give a cloudy solution. The mixture was filtered over a pad of silica gel and concentrated. The residue was dissolved in methylene chloride/methanol=1/1 solution and cooled to −78° C. To this solution was bubbled though ozone until the reaction mixture became a blue color. The reaction was warmed to 0° C. and added sodium borohydride (0.5 g) portion-wise. After stirring at 0° C. for 1 hour, the mixture was poured into water and extracted with ethyl acetate. The organic layer was washed with 1N NaOH$_{aq}$, brine, dried (MgSO₄), and concentrated under reduced pressure to afford crude alcohol. The alcohol was purified by silica gel (methylene chloride/ethyl acetate=1/1) to give desired alcohol. To a solution of alcohol in methylene chloride was added imidazole (0.4 g) and TBS—Cl (0.8 g) at 0° C. The mixture was stirred for 1 hour. The reaction was poured into 0.1 N HCl$_{aq}$ extracted with methylene chloride. The organic layer was washed with brine, dried (MgSO₄) and evaporated. The residue was purified by silica gel (100% methylene chloride) to give desired compound.

¹H NMR (CDCl₃): δ 8.61 (1H, d); 7.73 (1H, dd); 7.14 (1H, d); 3.97 (2H, t); 2.96 (2H, t); 0.36 (9H, s); −0.02 (6H, s).

Step B:

The desired compound was prepared by a procedure similar to the one described for Example 16, Steps A and B. This compound was purified by silica gel (hexanes/ethyl acetate=1/3).

¹H NMR (CHCl₃): δ 9.53 (1H, d); 8.54 (1H, dd); 8.35 (1H, d); 7.37 (1H, d); 7.07 (1H, dd); 6.56 (1H, d); 5.45 (2H, s); 4.11 (2H, t); 3.90 (3H, s); 3.18 (2H, t); 1.38 (9H, s).

LC-MS (M+H)=396.2.

Example 20

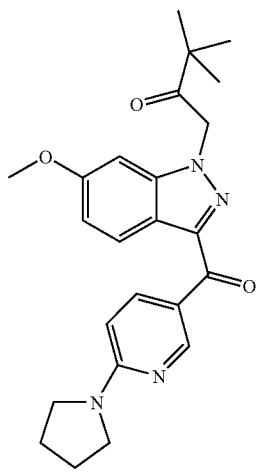

Step A:
To a solution of chloroiodopyridine (1.2 g), pyrrolidine (1.2 ml) and potassium carbonate (2.0 g) in DMF was heated 130° C. for 16 h. The mixture was cooled to RT and poured into ice/water to give crude solid material. The title compound was crystallized from hexanes/ethyl acetate (0.73 g).

$^1$H NMR (CDCl$_3$): 8.30 (1H, d); 7.62 (1H, dd); 6.23 (1H, d); 3.43 (4H, m); 2.03 (4H, m).

Step B:
To a solution of intermediate from Step A (274 mg) in THF was added isopropyl magnesium chloride (0.5 ml, 2N in diethyl ether) at −78° C. The mixture was warmed up to RT for a couple hours to complete iodide-magnesium exchange and re-cooled to −78° C. when Preparative Example 5 (110 mg) was added to the reaction mixture. The resulting solution was stirred at RT for 16 h and quenched with 1N NaOH, exacted with EtOAc. The organic layer was washed with brine, dried over magnesium sulfate and evaporated under vacuum. The residue was dissolved in 96% formic acid and heated to 100° C. for 16 h. After cooled to RT, the mixture was diluted with 1N NaOH to pH=9. The mixture was exacted with EtOAc, brine, dried over magnesium sulfate and evaporated under vacuum to give crude material.

Step C:
The title compound was prepared as described in Preparative Example 6, using chlorepinacolone instead of MOM—Cl. The final compound was purified by silica gel (hexanes/ethyl acetate 1/1).

$^1$H NMR (CDCl$_3$): 9.46 (1H, d); 8.40 (1H, d); 8.32 (1H, d); 7.00 (1H, dd); 6.53 (1H, d); 6.48 (1H, d); 5.43 (2H, s); 3.89 (3H, s); 3.63 (4H, br, s); 2.08 (4H, br, s); 1.37 (9H, s). LCMS (M+H)=421.4.

Example 21

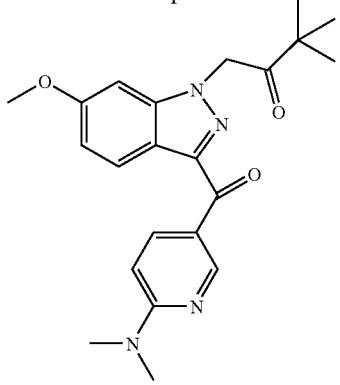

Step A: The title compound was prepared by a procedure similar to the one described for Example 20, Step A. The reaction used dimethylamine hydrogen chloride and potassium carbonate instead of pyrrolidine.

$^1$H NMR (CDCl$_3$): 8.31 (1H, d); 7.64 (1H, dd); 6.37 (1H, d); 3.08 (6H, s).

Step B:
The title compound was prepared by a procedure similar to the one described for Example 20, Step B and C by Using intermediate from Example 21, Step A instead of Example 20, Step A.

$^1$H NMR (CDCl$_3$): 9.41 (1H, d); 8.41 (1H, dd); 8.32 (1H, d); 7.01 (1H, dd); 6.60 (1H, d); 6.53 (1H, d); 5.42 (2H, s); 3.89 (3H, s); 3.24 (6H, s); 1.37 (9H, s).

LCMS (M+H)=395.4.

Example 22

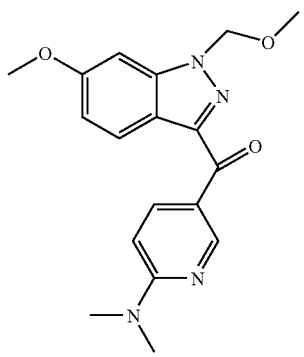

To a solution of intermediate from Example 21, Step A in THF was added isopropyl magnesium chloride (2N in diethyl ether) at −78° C. The mixture was warmed up to RT for a couple hours to complete iodide-magnesium exchange and re-cooled to −78° C. when Preparative Example 6 (110 mg) was added to the reaction mixture. The resulting solution was stirred at RT for 16 h and quenched with 1N NaOH, exacted with EtOAc. The organic layer was washed with brine, dried over magnesium sulfate and evaporated under vacuum. The title compound was purified by silica gel (methylene chloride/ethyl acetate=10/1).

$^1$H NMR (CDCl$_3$): 9.46 (1H, d); 8.45 (1H, dd); 8.31 (1H, d); 7.04 (1H, dd); 6.98 (1H, d); 6.62 (1H, d); 5.77 (2H, s); 3.94 (3H, s); 3.39 (3H, s); 3.25 (4H, s);

LCMS (M+H)=342.2.

Example 23

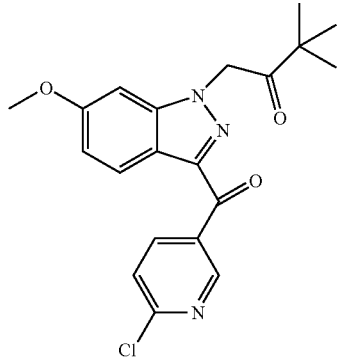

Step A:
To a solution of 2-chloro-5-iodopyridine in THF was added isopropyl magnesium chloride (0.5 ml, 2N in diethyl ether) at −78° C. The mixture was warmed up to RT for a couple hours to complete iodide-magnesium exchange and re-cooled to −78° C. when Intermediate from Preparative Example 2 was added to the reaction mixture. The resulting solution was stirred at RT for 16 h and quenched with 1N NaOH, exacted with EtOAc. The organic layer was washed with brine, dried over magnesium sulfate and evaporated under vacuum.

Step B:
The title compound was prepared as described in Preparative Example 6, using chloropinacolone instead of MOM—Cl. The final compound was purified by silica gel (hexanes/ethyl acetate=3/1).

$^1$H NMR (CDCl$_3$): 9.41 (1H, d); 8.53 (1H, dd); 8.33 (1H, d); 7.49 (1H, dd); 7.07 (1H, dd); 6.58 (1H, d); 5.43 (2H, s); 3.91 (3H, s); 1.37 (9H, s).
LCMS (M+H)=386.3.

Example 24

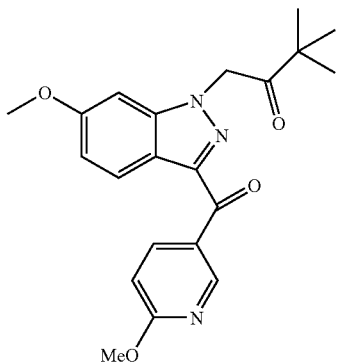

To a solution of intermediate from Example 23 in THF was added sodium methoxide (3 eq. 25% in methanol). The mixture was refluxed until reaction completed and quenched with 1N HCl. The mixture was extracted with ethyl acetate, brine, dried over magnesium sulfate and evaporated under vacuum. The residue was purified with silica gel (hexanes/ethyl acetate=2/1).

$^1$H NMR (CDCl$_3$): 9.35 (1H, d); 8.50 (1H, dd); 8.33 (1H, d); 7.04 (1H, dd); 6.86 (1H, d); 6.55 (1H, d); 5.43 (2H, s); 4.06 (3H, s); 3.90 (3H, s); 1.38 (9H, s).
LCMS (M+H)=386.3.

Example 25

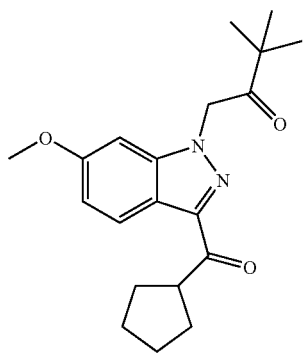

To 195 mg of NaH (60% dispersion in oil washed with hexane) was added DMF (10 mL) and Preparative Example 7 (597 mg, 2.44 mmol). The reaction stirred at room temperature for 30 min before 1-chloropinacolone (3.81 mL, 2.92 mmol) was added. After 20 min the reaction was quenched with H$_2$O and diluted with EtOAc. The aqueous layer was extracted with EtOAc and the combined organic layers were washed with H$_2$O, brine, dried over MgSO$_4$, and concentrated in vacuo. The crude material was purified via silica gel chromatography to yield.

$^1$H NMR (CDCl$_3$) δ: 1.361 (9H, s), 1.683 (2H, m), 1.788 (2H, m), 1.974 (4H, m), 3.872 (3H, s), 4.029 (1H, m), 5.372 (2H, s), 6.514 (1H, s), 6.986 (1H, d), 8.267 (1H, d).

Example 26

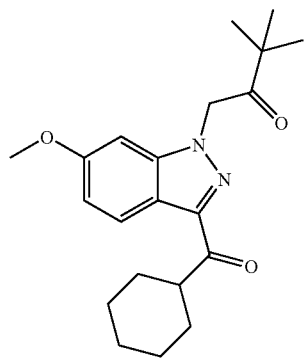

Using Preparative Example 8, this compound was prepared as described in Example 25. The title compound was purified via SiO$_2$ preparatory plate chromatography. $^1$H NMR (CDCl$_3$) δ: 1.285-1.575 (15H, m), 1.833 (2H, d), 1.994 (2H, d), 3.615 (1H, m), 3.860 (3H, s), 5.372 (2H, s), 6.490 (1H, s), 6.981 (1H, d), 8.254 (1H, d).

Example 27

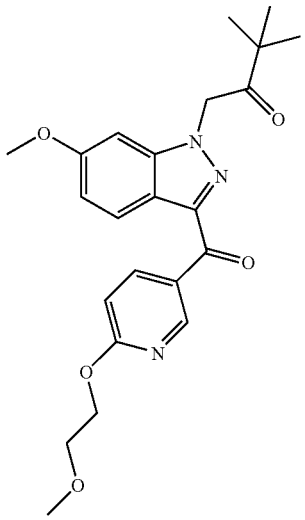

Using the intermediate from Example 23, this compound was prepared as described in Example 16, Step C but 2-methoxy-ethanol was used in place of ethylene glycol. The title compound was purified via SiO$_2$ preparatory plate chromatography. $^1$H NMR (CDCl$_3$) δ: 1.371 (9H, s), 3.475 (3H, s), 3.802 (2H, t), 3.889 (3H, s), 4.620 (2H, t), 5.424 (2H, s), 6.542 (1H, s), 6.923 (1H, d), 7.043 (1H, d), 8.337 (1H, d), 8.501 (1H, d), 9.299 (1H, s).

Example 28

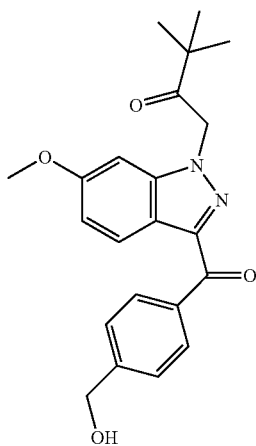

di-tert-butyl4-{[1-(3,3-dimethyl-2-oxobutyl)-6-methoxy-1-H-indazole-3-yl]carbonyl}hydroxyl Ethyl Benzyl Step 1

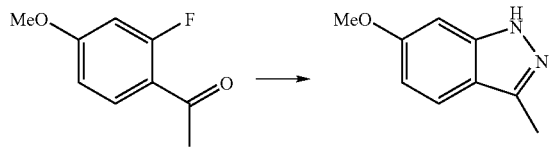

100 g of fluoro-acetophenone in 400 mL of ethylene glycol was stirred at room temperature with hydrazine (0.624 mol, 20 g) for 4 h after which the reaction mixture was heated to 150 C for 48 h. TLC analysis indicated complete reaction. Partitioned the reaction mixture into dichloromethane and brine. Dried organic phase over sodium sulphate and evaporated to a solid. Re-crystallized from hexane/dicholomethane gave indazole.

1H NMR (CDCL3): 7.5 (1H, d, 7.5 Hz); 6.8 (2H, m); 3.8 (3H, s); 2.55 (3H, s)

LCMS [M+H]=163

Step 2

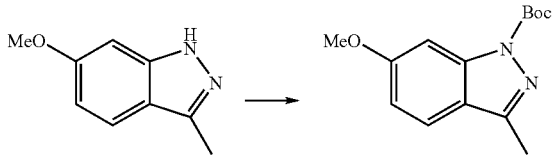

6-methoxy-3-methyl-1-H tert-butyl-6-methoxy-3-methyl-1-indazole-carboxylate Indazole 78 g of indazole was dissolved in 1 L of MeCN containing 1.1 equiv of tri-ethyl amine, 0.2 equiv of DMAP was cooled to −5 C; followed by slow addition of Boc2O (1.1 equiv) in 200 mL of MeCN. After 2 h of stirring the reaction at rt the reaction mixture was evaporated to an oil which was partitioned between EtOAc and brine, dried over sodium sulphate and evaporated. The residue was applied to a short SGC and eluted with 15% EtOAc in hexane. Evaporation gave product.

1H NMR (CDCL3): 7.6 (1H, bs); 7.42 (1H, d, J=7.5 Hz); 6.85 (1H, dd); 3.8 (3H, s); 2.5 (3H, s); 1.7 (9H, s)

LCMS [M+H]=263

Step 3

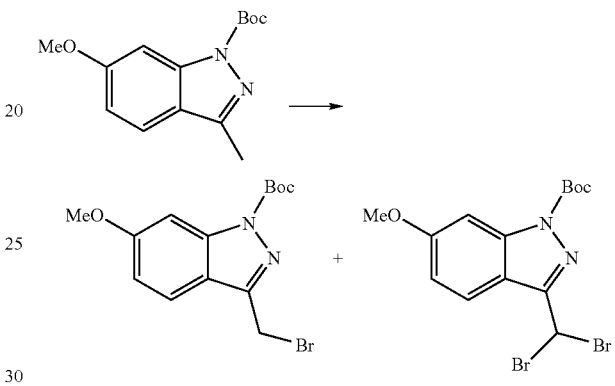

100 g of indazole was dissolved in 600 mL of CCl4, followed by addition of 1.1 equiv of NBS and 0.2 equiv of Bz2O. Reaction mix was vac-purged with argon and set to reflux for 5 h in presence of light from a sun lamp. Reaction mixture was filtered over a pad of SG and concentrated. Residual oil was purified over a short SGC. 85 g of pure bromide was obtained. Mixed fractions yielded di-bromo derivative mono-bromide: 1H NMR (CDCL3): 7.7 (1H, d, 7.5 Hz); 7.6 (1H bs); 6.95 (1H, dd); 4.7 (2H, s); 3.9 (3H, s); 1.7 (9H, s);

di-bromide: 1H NMR (CDCL3): 8.05 (1H, d, J=7.5 Hz); 7.6 (1H, bs); 7.0 (1H, dd); 6.85 (1H, s); 3.9 (3H, s); 1.7 (9-H, s);

Step 4

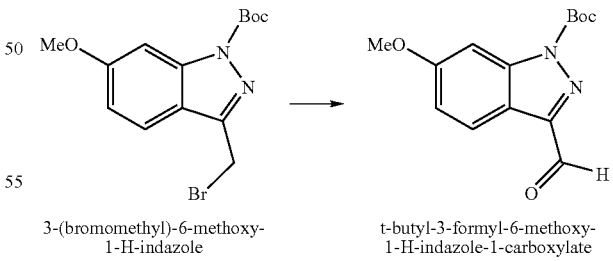

3-(bromomethyl)-6-methoxy-1-H-indazole    t-butyl-3-formyl-6-methoxy-1-H-indazole-1-carboxylate 5 g of bromide was dissolved in 10 mL of DMSO, cooled to 0 C followed by addition of 2.5 equiv of TMANO (trimethyl amine N-oxide). Reaction was stirred for 0.5 h then a standard work-up and SG pad filteration gave desired product quantitatively. LCMS [M+H]=277

1H NMR (CDCL3): 10.2 (1H, s); 8.1 (1H, d, J=7.5 Hz); 7.6 (1H, bs); 7.0 (1H, dd); 3.9 (3H, s); 1.7 (9H, s);

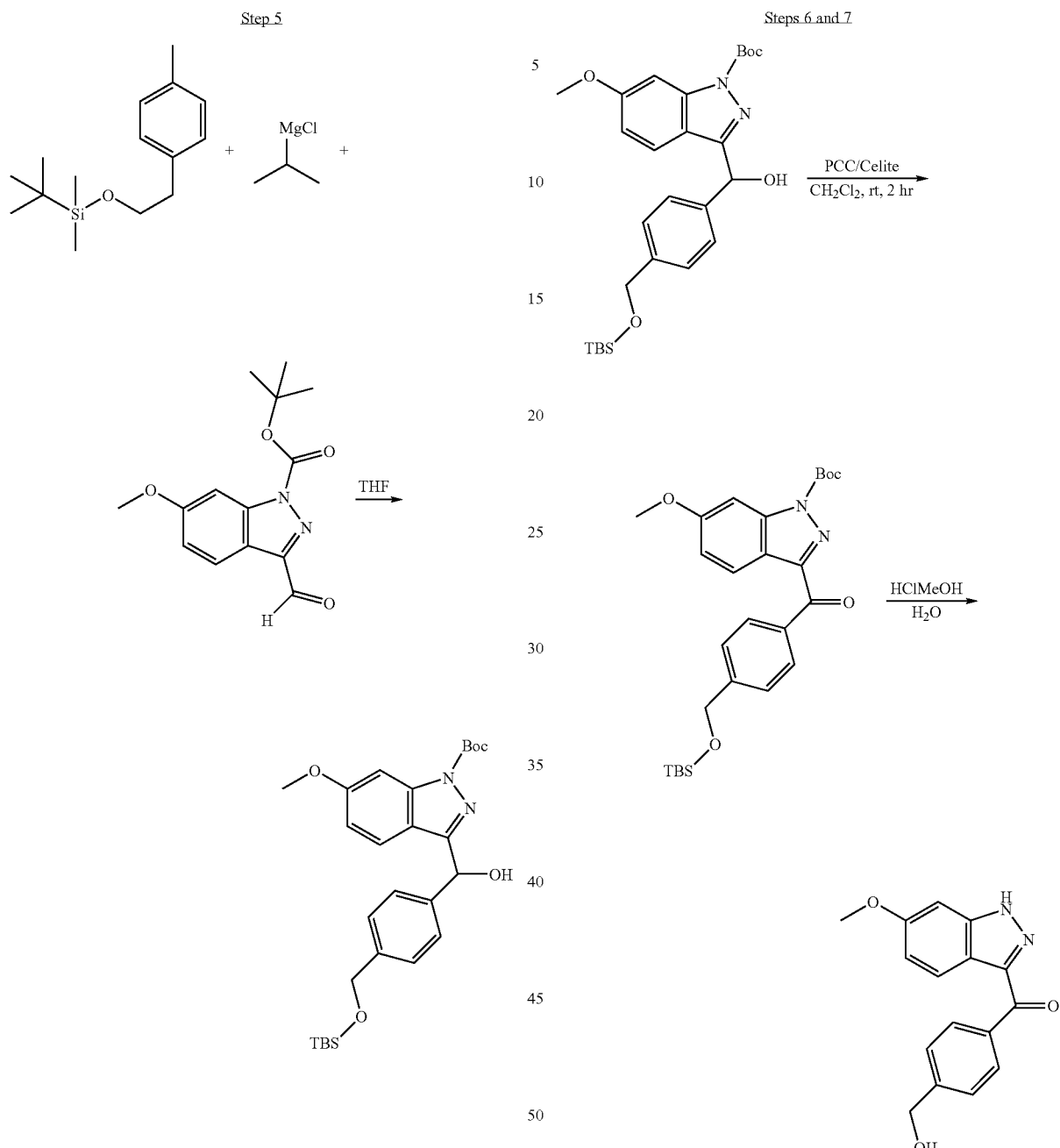

Glasswares were Flame Dried Under High Vacuum

To neat iodo-benzyl alcohol derivative (3.6 g, 110 mmol) in the flask was slowly added isopropylMgCl (5 mL, 2M solution). After stirring at rt for 2 hr, indazole derivative (1.1 g, 4 mmol) in 15 mL THF was added. The reaction mixture was stirred at rt for 2 hr. LC-MS showed the reaction was complete. Pour the reaction mixture into 30 mL saturated NH4Cl, followed by adding 40 mL ether. The organic layer was separated, the aqueous layer was extracted by ether (40 mL). The combined organic layers were washed with saturated K2CO3 (2×30 mL), water (40 mL) and brine (20 mL). The solvent was removed, the residue was used for next step reaction without further purification. LCMS [M+H]=499

To a solution of indazole (crude from step 5) in 20 mL dichloromethane was added 5 g celite and 4.3 g of PCC (MW 215.56, ~2 eq). The reaction mixture was stirred at rt for 2 hr. LC-MS showed the reaction was completed LCMS [M+H]= 497. The reaction mixture was filtered.

The solvent was removed, the residue was dissolved in 10 mL MeOH, and added 20 mL 2N HCl. After stirring for 1 hr at rt LCMS and TLC analysis indicated complete reaction. The reaction mixture was extracted with EtOAc (2×30 mL). The solvent was removed, the residue was used for next step reaction without further purification. LCMS [M+H]=283

Step 8

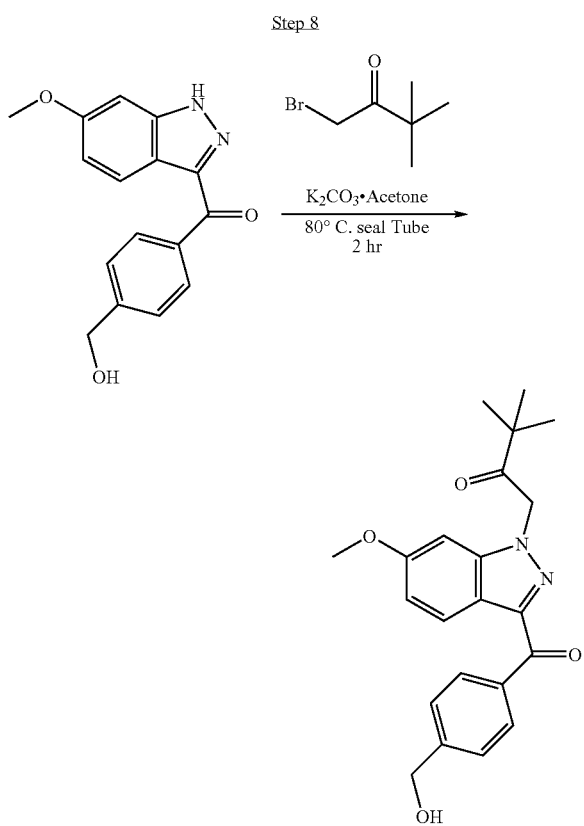

To a solution of indazole (342 mg crude prod from step 7, ~10 mmol)) in 15 mL, acetone was added 1.5 g of K2CO3 and 1.5 mL Bromopinacolone (Mw179.06, d1.326, 2.0 g, 11 mmol). The reaction mixture was stirred at 80° C. in a sea) tube for 2 hr. After filtered off salts, the solvent was removed, the residue was purified by HPFC to give white solid product.

1H NMR (CDCL3)=8.3 (3H, m); 7.5 (1H, d, J=7.5 Hz); 7.05 (1H, dd); 7.6 (1H, bs); 5.4 (2H, s); 4.8 (2H, bs); 3.9 (3H, s); 1.38 (9H, s)

LCMS [M+H]=381

Functional Assays

A. Maxi-K Channel

The identification of inhibitors of the Maxi-K channel can be accomplished using Aurora Biosciences technology, and is based on the ability of expressed Maxi-K channels to set cellular resting potential after transient transfection of both α and β subunits of the channel in TsA-201 cells. In the absence of inhibitors, cells display a hyperpolarized membrane potential, negative inside, close to $E_K$ (−80 mV) which is a consequence of the activity of the Maxi-K channel. Blockade of the Maxi-K channel will cause cell depolarization. Changes in membrane potential can be determined with voltage-sensitive fluorescence resonance energy transfer (FRET) dye pairs that use two components, a donor coumarin ($CC_2DMPE$) and an acceptor oxanol ($DiSBAC_2(3)$). Oxanol is a lipophilic anion and distributes across the membrane according to membrane potential. Under normal conditions, when the inside of the cell is negative with respect to the outside, oxanol is accumulated at the outer leaflet of the membrane and excitation of coumarin will cause FRET to occur. Conditions that lead to membrane depolarization will cause the oxanol to redistribute to the inside of the cell, and, as a consequence, to a decrease in FRET. Thus, the ratio change (donor/acceptor) increases after membrane depolarization.

Transient transfection of the Maxi-K channel in TsA-201 cells can be carried out as previously described (Hanner et al. (1998) J. Biol. Chem. 273, 16289-16296) using FUGENE6™ as the transfection reagent. Twenty four hours after transfection, cells are collected in $Ca^{2+}$—$Mg^{2+}$-free Dulbecco's phosphate-buffered saline (D-PBS), subjected to centrifugation, plated onto 96-well poly-d-lysine coated plates at a density of 60,000 cells/well, and incubated overnight. The cells are then washed 1× with D-PBS, and loaded with 100 μl of 4 μM $CC_2DMPE$-0.02% pluronic-127 in D-PBS. Cells are incubated at room temperature for 30 min in the dark. Afterwards, cells are washed 2× with D-PBS and loaded with 100 μl of 6 μM $DiSBAC_2(3)$ in (mM): 140 NaCl, 0.1KCl, $2CaCl_2$, $1MgCl$, 0 Hepes-NaOH, pH, 7.4, 10 glucose. Test compounds are diluted into this solution, and added it the same time. Cells are incubated at room temperature for 30 min in the dark.

Plates are loaded onto a voltage/ion probe reader (VIPR) instrument, and the fluorescene emission of both $CC_2DMPE$ and $DiSBAC_2(3)$ are recorded for 10 sec. At this point, 100 μl of high-potassium solution (mM): 140KCl, $2CaCl_2$, $1MgCl_2$, 20 Hepes-KOH, pH 7.4, 10 glucose are added and the fluorescence emission of both dyes recorded for additional 10 sec. The ratio $CC_2DMPE/DiSBAC_2(3)$, before addition of high-potassium solution equals 1. In the absence of any inhibitor, the ratio after addition of high-potassium solution varies between 1.65-2.0. When the Maxi-K channel has been completely inhibited by either a known standard of test compound, this ratio remains at 1. It is possible, therefore, to titrate the activity of a Maxi-K channel inhibitor by monitoring the concentration-dependent change in the fluorescence ratio.

The compounds of this invention were found to cause concentration-dependent inhibition of the fluorescence ratio with $IC_{50}$'s in the range of about 1 nM to about 20 μM, more preferably from about 10 nM to about 500 nM.

B. Electrophysiological Assays of Compound Effects on High-Conductance Calcium-Activated Potassium Channels Human Non-Pigmented Ciliary Epithelial Cells The activity of high-conductance calcium-activated potassium (maxi-K) channels in human non-pigmented ciliary epithelial cells was determined using electrophysiological methods. Currents through maxi-K channels were recorded in the inside-out configuration of the patch clamp technique, where the pipette solution faces the extracellular side of the channel and the bath solution faces the intracellular side. Excised patches contained one to about fifty maxi-K channels. Maxi-K channels were identified by their large single channel conductance (250-300 pS), and by sensitivity of channel gating to membrane potential and intracellular calcium concentration. Membrane currents were recorded using standard electrophysiological techniques. Glass pipettes (Garner 7052) were pulled in two stages with a Kopf puller (model 750), and electrode resistance was 1-3 megohms when filled with saline. Membrane currents were recorded with EPC9 (HEKA Instruments) or Axopatch 1D (Axon Instruments) amplifiers, and digital conversion was done with ITC-16 interfaces (Instrutech Corp). Pipettes were filled with (mM); 150KCl, 10 Hepes, $1MgCl_2$, $0.01CaCl_2$, 3.65KOH, pH 7.20. The bath (intracellular) solution was identical, except, in some cases, calcium was removed, 1 mM EGTA was added and 20 mM KCl was replaced with 20 mM KF to eliminate calcium to test for calcium sensitivity of channel gating. Drugs were applied to the intracellular side of the channel by bath perfusion.

Human non-pigmented ciliary epithelial cells were grown in tissue culture as described (Martin-Vasallo, P., Ghosh, S., and Coca-Prados, M., 1989. J. Cell. Physiol. 141, 243-252), and plated onto glass cover slips prior to use. High resistance seals (>1 Gohm) were formed between the pipette and cell surface, and inside out patches were excised. Maxi-K channels in the patch were identified by their gating properties; channel open probability increased in response to membrane depolarization and elevated intracellular calcium. In patches used for pharmacological analysis, removing intracellular calcium eliminated voltage-gated currents. Maxi-K currents were measured after depolarizing voltage steps or ramps that caused channel opening.

The compounds of this invention were applied to the intracellular side of the channel in appropriate concentrations (0.001 to 100 μM). The compounds reduced channel open probability, and this effect was reversed upon washout of compounds from the experimental chamber. The IC50 for block of maxi-K channels under these conditions for the compounds of this invention ranged from about 0.5 nM to about 10 μM.

What is claimed is:

1. A method for treating ocular hypertension or glaucoma comprising administration to a patient in need of such treatment a therapeutically effective amount of a compound of structural formula I:

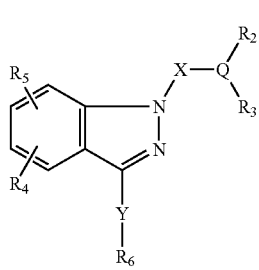

Formula I or a pharmaceutically acceptable salt, enantiomer, diastereomer or mixture thereof:
wherein,
R represents hydrogen, or $C_{1-6}$ alkyl;
X represents —$(CHR_7)_p$—, —$(CHR_7)_p CO$—;
Y represents —$CO(CH_2)_n$—, $CH_2$, or —$CH(OR)$—;
Q represents $CR_y$;
$R_y$ represents H, or $C_{1-6}$ alkyl;
$R_w$ represents H, $C_{1-6}$ alkyl, —$C(O)C_{1-6}$ alkyl, —$C(O)$ $OC_{1-6}$ alkyl, —$SO_2N(R)_2$, —$SO_2C_{1-6}$ alkyl, —$SO_2$ $C_{6-10}$ aryl, $NO_2$, $CN$ or —$C(O)N(R)_2$;
$R_2$ represents hydrogen, $C_{1-10}$ alkyl, OH, $C_{2-6}$ alkenyl, $C_{1-6}$ alkylSR, —$(CH_2)_n$—$O(CH_2)_m OR$, —$(CH_2)_n C_{1-6}$ alkoxy, —$(CH_2)_n C_{3-8}$ cycloalkyl, —$(CH_2)_n C_{3-10}$ heterocyclyl, —$N(R)_2$, —$COOR$, or —$(CH_2)_n C_{6-10}$ aryl, said alkyl, heterocyclyl, or aryl optionally substituted with 1-3 groups selected from $R^a$;
$R_3$ represents hydrogen, $C_{1-10}$ alkyl, —$(CH_2)_n C_{3-8}$ cycloalkyl, —$(CH_2)_n C_{3-10}$ heterocyclyl, —$(CH_2)_n$ COOR, —$(CH_2)_n C_{6-10}$ aryl, —$(CH_2)_n NHR_8$, —$(CH_2)_n$ $N(R)_2$, —$(CH_2)_n N(R_8)_2$, —$(CH_2)_n NHCOOR$, —$(CH_2)_n$ $N(R_8)CO_2R$, —$(CH_2)_n N(R_8)COR$, —$(CH_2)_n$ $NHCOR$, —$(CH_2)_n CONH(R_8)$, aryl, —$(CH_2)_n C_{1-6}$ alkoxy, $CF_3$, —$(CH_2)_n SO_2R$, —$(CH_2)_n SO_2N(R)_2$, —$(CH_2)_n CON(R)_2$, —$(CH_2)_n CONHC(R)_3$, —$(CH_2)_n$ $CONHC(R)_2CO_2R$, —$(CH_2)_n COR_8$, nitro, cyano or halogen, said alkyl, alkoxy, heterocyclyl, or aryl optionally substituted with 1-3 groups of $R^a$;

or $R_2$ and $R_3$ taken together with the intervening Q form a 3-10 membered carbocyclic or heterocyclic carbon ring optionally interrupted by 1-2 atoms of O, S, C(O) or NR, and optionally having 1-4 double bonds, and optionally substituted by 1-3 groups selected from $R^a$;
or $R_2$ and $R_3$ taken together with the intervening Q represent OR;
$R_4$ and $R_5$ independently represent hydrogen, $C_{1-6}$ alkoxy, OH, $C_{1-6}$ alkyl, COOR, $SO_q C_{1-6}$ alkyl, $COC_{1-6}$ alkyl, $SO_3H$, —$O(CH_2)_n N(R)_2$, —$O(CH_2)_n CO_2R$, —$OPO$ $(OH)_2$, $CF_3$, $OCF_3$—$N(R)_2$, nitro, cyano, $C_{1-6}$ alkylamino, or halogen; and
$R_6$ represents hydrogen, $C_{1-10}$ alkyl, —$(CH_2)_n C_{6-10}$ aryl, $NR_c R_d$, —$NR(CH_2)_n C_{6-10}$ aryl, —$N((CH_2)_n C_{6-10}$ aryl), —$(CH_2)_n C_{3-10}$ heterocyclyl, —$NR(CH_2)_n C_{3-10}$ heterocyclyl, —$N((CH_2)_n C_{3-10}$ heterocyclyl$)_2$ ($C_{6-10}$ aryl) O—, —$(CH_2)_n C_{3-8}$ cycloalkyl, —$COOR$, —$C(O)$ $CO_2R$, said aryl, heterocyclyl and alkyl optionally substituted with 1-3 groups selected from $R^a$, wherein the $R^a$(s) can be attached to any carbon atom or heteroatom selected from N and 5;
$R_c$ and $R_d$ independently represent H, $C_{1-6}$ alkyl, $C_{2-6}$ alkenyl, $C_{1-6}$ alkylSR, —$(CH_2)_n O(CH_2)_m OR$, —$(CH_2)_n$ $C_{1-6}$ alkoxy, or —$(CH_2)_n C_{3-8}$ cycloalkyl;
or $R_c$ and $R_d$ taken together with the intervening N atom form a 4-10 membered heterocyclic carbon ring optionally interrupted by 1-2 atoms of O, S, C(O) or NR, and optionally having 1-4 double bonds, and optionally substituted by 1-3 groups selected from $R^a$;
$R_7$ represents hydrogen, $C_{1-6}$ alkyl, —$(CH_2)_n COOR$ or —$(CH_2)_n N(R)_2$,
$R_8$ represents —$(CH_2)_n C_{3-8}$ cycloalkyl, —$(CH_2)_{n\ 3-10}$ heterocyclyl, $C_{1-6}$ alkoxy or —$(CH_2)_n C_{5-10}$ heteroaryl, —$(CH_2)_n C_{6-10}$ aryl said heterocyclyl, aryl or heteroaryl optionally substituted with 1-3 groups selected from $R^a$;
$R^a$ represents F, Cl, Br, I, $CF_3$, $N(R)_2$, $NO_2$, $CN$, —$O$—, —$COR_8$, —$CONHR_8$, —$CON(R_8)_2$, —$O(CH_2)_n$ COOR, —$NH(CH_2)_n OR$, —$COOR$, $OCF_3$, $CF_2CH_2OR$, —$NHCOR$, —$SO_2R$, —$SO_2NR_2$, —$SR$, ($C_1$-$C_6$ alkyl)O—, —$(CH_2)_n O(CH_2)_m OR$, —$(CH_2)_n$ $C_{1-6}$ alkoxy, (aryl)O—, —$(CH_2)_n OH$, ($C_1$-$C_6$ alkyl)S $(O)_m$—, $H_2N$—$C(NH)$—, ($C_1$-$C_6$ alkyl)$C(O)$—, ($C_1$-$C_6$ alkyl)$OC(O)NH$—, —($C_1$-$C_6$ alkyl)$NR_w(CH_2)_n C_{3-10}$ heterocyclyl-$R_w$, —($C_1$-$C_6$ alkyl)$O(CH_2)_n C_{3-10}$ heterocyclyl-$R_w$, —($C_1$-$C_6$ alkyl)$S(CH_2)_n C_{3-10}$ heterocyclyl-$R_w$, —($C_1$-$C_6$ alkyl)-$C_{3-10}$ heterocyclyl-$R_w$, —$(CH_2)_n$ —$Z^1$—$C(=Z^2)N(R)_2$, —($C_{2-6}$ alkenyl)$NR_w(CH_2)_n$ $C_{3-10}$ heterocyclyl-$R_w$, —($C_{2-6}$ alkenyl)$O(CH_2)_n C_{3-10}$ heterocycyl-$R$, —($C_{2-6}$ alkenyl)$S(CH_2)_n C_{3-10}$ heterocyclyl-$R_w$, —($C_{2-6}$ alkenyl)-$C_{3-10}$ heterocyclyl-$R_w$, —($C_{2-6}$ alkenyl)-$Z^1$—$C(=Z^2)N(R)_2$, —$(CH_2)_n SO_2R$, —$(CH_2)_n SO_3H$, —$(CH_2)_n PO(OR)_2$, $C_{3-10}$cycloalkyl, $C_{6-10}$ aryl, $C_{3-10}$ heterocyclyl, $C_{2-6}$ alkenyl, and $C_1$-$C_{10}$ alkyl, said alkyl, alkenyl, alkoxy, heterocyclyl and aryl optionally substituted with 1-3 groups selected from $C_1$-$C_6$ alkyl, halogen, $(CH_2)_n OH$, CN, $NO_2$, $CON(R)_2$ and COOR;
$Z^1$ and $Z^2$ independently represents $NR_w$, O, $CH_2$, or S;
m is 0-3;
n is 0-3;
p is 0-3 and
q is 0-2.

2. A method for treating macular edema, macular degeneration, increasing retinal and optic nerve head blood velocity, increasing retinal and optic nerve oxygen tension, and/or a neuroprotective effect comprising administration to a patient in need of such treatment a pharmaceutically effective amount of a compound of structural formula I:

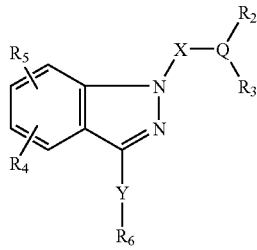

Formula I or a pharmaceutically acceptable salt, enantiomer, diastereomer or mixture thereof:
wherein, R represents hydrogen, or $C_{1-6}$ alkyl;

X represents —$(CHR_7)_p$—, —$(CHR_7)_p CO$;

Y represents —$CO(CH_2)_n$—, $CH_2$, or —$CH(OR)$—;

Q represents $CR^y$;

$R^y$ represents H, or $C_{1-6}$ alkyl;

$R_w$ represents H, $C_{1-6}$ alkyl, —$C(O)C_{1-6}$ alkyl, —$C(O)OC_{1-6}$ alkyl, —$SO_2N(R)_2$, —$SO_2C_{1-6}$ alkyl, —$SO_2 C_{6-10}$ aryl, $NO_2$, CN or —$C(O)N(R)_2$;

$R_2$ represents hydrogen, $C_{1-10}$ alkyl, OH, $C_{2-6}$ alkenyl, $C_{1-6}$ alkylSR, —$(CH_2)_n$—$O(CH_2)_m OR$, —$(CH_2)_n C_{1-6}$ alkoxy, —$(CH_2)_n C_{3-8}$ cycloalkyl, —$(CH_2)_n C_{3-10}$ heterocyclyl, —$N(R)_2$, —COOR, or —$(CH_2)_n C_{6-10}$ aryl, said alkyl, heterocyclyl, or aryl optionally substituted with 1-3 groups selected from $R^a$;

$R_3$ represents hydrogen, $C_{1-10}$ alkyl, —$(CH_2)_n C_{3-8}$ cycloalkyl, —$(CH_2)_n C_{3-40}$ heterocyclyl, —$(CH_2)_n$ COOR, —$(CH_2)_n C_{6-10}$ aryl, —$(CH_2)_n NHR_8$, —$(CH_2)_n N(R)_2$, —$(CH_2)_n N(R_8)_2$, —$(CH_2)_n NHCOOR$, —$(CH_2)_n N(R_8)CO_2 R$, —$(CH_2)_n N(R_8)COR$, —$(CH_2)_n NHCOR$, —$(CH_2)_n CONH(R_8)$, aryl, —$(CH_2)_n C_{1-6}$ alkoxy, $CF_3$, —$(CH_2)_n SO_2 R$, —$(CH_2)_n SO_2 N(R)_2$, —$(CH_2)_n CON(R)_2$, —$(CH_2)_n CONHC(R)_3$, —$(CH_2)_n CONHC(R)_2 CO_2 R$, —$(CH_2)_n COR_8$, nitro, cyano or halogen, said alkyl, alkoxy, heterocyclyl, or aryl optionally substituted with 1-3 groups of $R^a$;

or $R_2$ and $R_3$ taken together with the intervening Q form a 3-10 membered carbocyclic or heterocyclic carbon ring optionally interrupted by 1-2 atoms of O, S, C(O) or NR, and optionally having 1-4 double bonds, and optionally substituted by 1-3 groups selected from $R^a$;

or $R_2$ and $R_3$ taken together with the intervening Q represent OR;

$R_4$ and $R_5$ independently represent hydrogen, $C_{1-6}$ alkoxy, OH, $C_{1-6}$ alkyl, COOR, $SO_q C_{1-6}$ alkyl, $COC_{1-6}$ alkyl, $SO_3 H$, —$O(CH_2)_n N(R)_2$, —$O(CH_2)_n CO_2 R$, —OPO$(OH)_2$, $CF_3$, $OCF_3$—$N(R)_2$, nitro, cyano, $C_{1-6}$ alkylamino, or halogen; and $R_6$ represents hydrogen, $C_{1-10}$ alkyl, —$(CH_2)_n C_{6-10}$ aryl, $NR_c R_d$, —$NR(CH_2)_n C_{6-10}$ aryl, —$N((CH_2)_n C_{6-10}$ aryl$)_2$, —$(CH_2)_n C_{3-10}$ heterocyclyl, —$NR(CH_2)_n C_{3-10}$ heterocyclyl, —$N((CH_2)_n C_{3-10}$ heterocyclyl$)_2 (C_{6-10}$ aryl)O—, —$(CH_2)_n C_{3-8}$ cycloalkyl, —COOR, —C(O)CO$_2$R, said aryl, heterocyclyl and alkyl optionally substituted with 1-3 groups selected from $R^a$, wherein the $R^a$(s) can be attached to any carbon atom or heteroatom selected from N and S;

$R_c$ and $R_d$ independently represent H, C1-6 alkyl, $C_{2-6}$ alkenyl, $C_{1-6}$ alkylSR, —$(CH_2)_n O(CH_2)_m OR$, —$(CH_2)_n C_{1-6}$ alkoxy, or —$(CH_2)_n C_{3-8}$ cycloalkyl;

or $R_c$ and $R_d$ taken together with the intervening N atom form a 4-10 membered heterocyclic carbon ring optionally interrupted by 1-2 atoms of O, S, C(O) or NR, and optionally having 1-4 double bonds, and optionally substituted by 1-3 groups selected from $R^a$;

$R_7$ represents hydrogen, $C_{1-6}$ alkyl, —$(CH_2)_n COOR$ or —$(CH_2)_n N(R)_2$, $R_8$ represents —$(CH_2)_n C_{3-8}$ cycloalkyl, —$(CH_2)_{n\ 3-10}$ heterocyclyl, $C_{1-6}$ alkoxy or —$(CH_2)_n C_{51}o$ heteroaryl, —$(CH_2)_n C_{6-10}$ aryl said heterocyclyl, aryl or heteroaryl optionally substituted with 1-3 groups selected from $R^a$;

$R^a$ represents F, Cl, Br, I, $CF_3$, $N(R)_2$, $NO_2$, CN, —O—, —$COR_8$, —$CONHR_8$, —$CON(R_8)_2$, —$O(CH_2)_n COOR$, —$NH(CH_2)_n OR$, COOR, —$OCF_3$, $CF_2 CH_2 OR$, NHCOR, $SO_2 R$, $SO_2 NR_2$, SR, $(C_1\text{-}C_6$ alkyl)O—, —$(CH_2)_n$—$O(CH_2)_m OR$, —$(CH_2)_n C_{1-6}$ alkoxy, (aryl)O—, —$(CH_2)_n OH$, $(C_1\text{-}C_6$ alkyl)S$(O)_m$—, $H_2 N$—C(NH)—, $(C_1\text{-}C_6$ alkyl)C(O)—, $(C_1\text{-}C_6$ alkyl)OC(O)NH—, —$(C_1\text{-}C_6$ alkyl)NR$_w$(CH$_2$)$_n$C$_{3-10}$ heterocyclyl-R$_w$, —$(C_1\text{-}C_6$ alkyl)O(CH$_2$)$_n$C$_{3-10}$ heterocyclyl-R$_w$, —$(C_1\text{-}C_6$ alkyl)S(CH$_2$)$_n$C$_{3-10}$ heterocyclyl-R$_w$, —$(C_1\text{-}C_6$ alkyl)-C$_{3-10}$ heterocyclyl-R$_w$, —(CH$_2$)$_n$—Z$^1$C(=Z$^2$)N(R)$_2$, —$(C_{2-6}$ alkenyl)NR$_w$(CH$_2$)$_n$C$_{3-10}$ heterocyclyl-R$_w$, —$(C_{2-6}$ alkenyl)O(CH$_2$)$_n$C$_{3-10}$ heterocyclyl-R$_w$, —$(C_{2-6}$ alkenyl)S(CH$_2$)$_n$C$_{3-10}$ heterocyclyl-R$_w$, —$(C_{2-6}$ alkenyl)-C$_{3-10}$ heterocyclyl-R$_w$, —$(C_{2-6}$ alkenyl)-Z$^1$—C(=Z$^2$)N(R)$_2$, —$(CH_2)_n SO_2 R$, —$(CH_2)_n SO_3 H$, —$(CH_2)_n PO(OR)_2$, $C_{3-10}$ cycloalkyl, $C_{6-10}$ aryl, $C_{3-10}$ heterocyclyl, $C_{2-6}$ alkenyl, and $C_1\text{-}C_{10}$ alkyl, said alkyl, alkenyl, alkoxy, heterocyclyl and aryl optionally substituted with 1-3 groups selected from $C_1\text{-}C_6$ alkyl, halogen, $(CH_2)_n OH$, CN, $NO_2$, $CON(R)_2$ and COOR;

$Z^1$ and $Z^2$ independently represents NR, O, $CH_2$, or S;

m is 0-3;

n is 0-3;

p is 0-3 and q is 0-2.

3. The method in accordance with claim 1 wherein the compound is represented by:

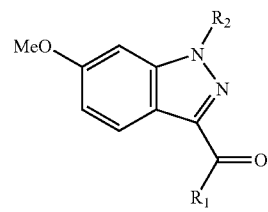

wherein:

| R1 | R2 |
|---|---|
| 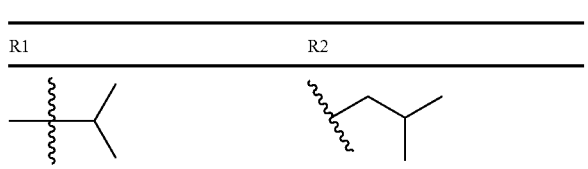 | |

-continued
| R1 | R2 |
|---|---|
| 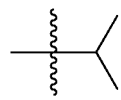 | 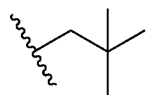 |
|  | 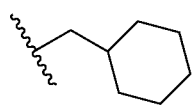 |
| 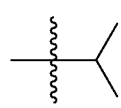 | 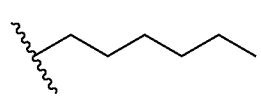 |
|  | 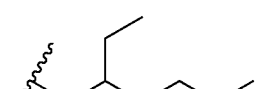 |
|  | 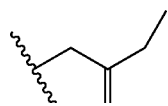 |
|  | 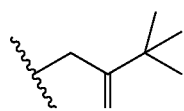 |
| 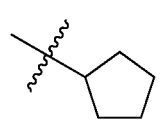 | 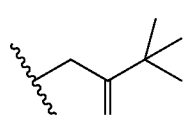 |
-continued
| R1 | R2 |
|---|---|
| 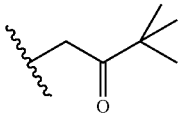  x = CH, N; p = 0-1; n = 0-3 | 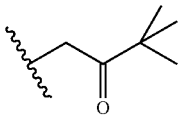 |
| —(CH2)$_n$OH  n = 0-3 | 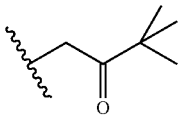 |
or a pharmaceutically acceptable salt, enantiomer, diastereomer or mixture thereof.
4. The method according to claim 3 wherein the compound is
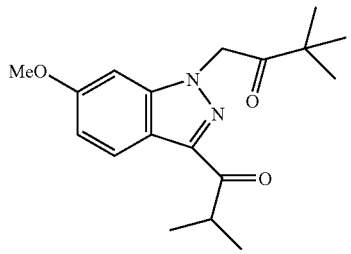
or a pharmaceutically acceptable salt, enantiomer, diastereomer or mixture thereof.
\* \* \* \* \*